United States Patent
Uplinger, II et al.

(10) Patent No.: US 10,448,864 B1
(45) Date of Patent: Oct. 22, 2019

(54) APPARATUS AND METHOD TO IDENTIFY AND MEASURE GAS CONCENTRATIONS

(71) Applicant: NOKOMIS, INC., Charleroi, PA (US)

(72) Inventors: James Robert Uplinger, II, Cranberry Township, PA (US); Robert M. Nichol, Washington, PA (US); Walter John Keller, Bridgeville, PA (US)

(73) Assignee: NOKOMIS, INC., Charleroi, PA (US)

(*) Notice: Subject to any disclaimer, the term of this patent is extended or adjusted under 35 U.S.C. 154(b) by 214 days.

(21) Appl. No.: 15/459,494

(22) Filed: Mar. 15, 2017

Related U.S. Application Data

(60) Provisional application No. 62/463,126, filed on Feb. 24, 2017.

(51) Int. Cl.
| | | |
|---|---|---|
| *G01R 31/34* | (2006.01) | |
| *A61B 5/08* | (2006.01) | |
| *G01N 22/00* | (2006.01) | |
| *G01N 33/497* | (2006.01) | |

(52) U.S. Cl.
CPC ............. *A61B 5/082* (2013.01); *G01N 22/00* (2013.01); *G01N 33/497* (2013.01)

(58) Field of Classification Search
CPC ................ G01R 19/0092; G01R 15/18; G01R 31/2805; G01R 31/34; G01R 35/02; G01R 3/00; G01N 22/00; G01N 33/497; A61B 5/082
USPC .... 324/639, 500, 512, 76.65, 536, 541, 122, 324/535, 523, 532, 501, 547, 115, 117 R, 324/520, 551, 242, 127, 133, 534; 702/189, 58, 59, 205, 258, 207, 64
See application file for complete search history.

(56) References Cited

U.S. PATENT DOCUMENTS

| | | | |
|---|---|---|---|
| 3,028,596 A | 4/1962 | McGillem et al. | |
| 3,599,211 A | 8/1971 | Mardon | |
| 3,631,484 A | 12/1971 | Angenblick | |
| 3,707,672 A | 12/1972 | Mlller et al. | |
| 3,732,567 A | 5/1973 | Low et al. | |

(Continued)

FOREIGN PATENT DOCUMENTS

| | | |
|---|---|---|
| CA | 2265304 | 3/1999 |
| DE | 102005040494 | 3/2007 |

(Continued)

OTHER PUBLICATIONS

Ashwin Lakshminarasimhan; Electromagnetic Side-Channel Analysis for Hardware and Software Watermarking; Sep. 2011; submitted to the Graduate School of the University of Massachusetts Amherst.

(Continued)

*Primary Examiner* — Jermele M Hollington
*Assistant Examiner* — Taqi R Nasir
(74) *Attorney, Agent, or Firm* — AP Patents

(57) ABSTRACT

A method and apparatus is provided for the analysis of gaseous compounds, especially for determining the concentration of a gas or gases in a gas mixture by microwave spectroscopy. Microwave radiation is generated at one or more frequencies the gas is most responsive to, transmitted by antenna, passed through the gas under test, received by antenna, and the absorption and/or reflection of the microwave radiation is measured by means such as digitization and analysis using the FFT spectrum versus energy response generated, the response subsequently used to calculate the gas concentration.

17 Claims, 10 Drawing Sheets

(56) References Cited

U.S. PATENT DOCUMENTS

| | | | |
|---|---|---|---|
| 3,795,911 A | 3/1974 | Hammack | |
| 3,911,435 A | 10/1975 | Mardon et al. | |
| 3,930,734 A | 1/1976 | Holly et al. | |
| 3,973,186 A * | 8/1976 | Uehara | G01N 22/005 |
| | | | 324/636 |
| 4,035,797 A | 7/1977 | Nagy | |
| 4,053,891 A | 10/1977 | Opitz | |
| 4,058,804 A | 11/1977 | Sawada et al. | |
| 4,121,214 A | 10/1978 | Marinaccio et al. | |
| 4,239,388 A | 12/1980 | Green | |
| 4,303,910 A | 12/1981 | McCann | |
| 4,351,029 A | 9/1982 | Maxey et al. | |
| 4,380,172 A | 4/1983 | Imam et al. | |
| 4,442,494 A | 4/1984 | Fromson et al. | |
| 4,496,900 A | 1/1985 | Di Stefano et al. | |
| 4,614,945 A | 9/1986 | Brunius et al. | |
| 4,648,124 A | 3/1987 | Mantovani et al. | |
| 4,650,333 A | 3/1987 | Crabb et al. | |
| 4,658,245 A | 4/1987 | Dye et al. | |
| 4,726,224 A | 2/1988 | D'Ausilio | |
| 4,827,414 A | 5/1989 | Christianson et al. | |
| 4,972,699 A | 11/1990 | Berger et al. | |
| 5,006,788 A | 4/1991 | Goulette et al. | |
| 5,020,411 A | 6/1991 | Rowan | |
| 5,028,866 A | 7/1991 | Wiese | |
| 5,057,782 A | 10/1991 | Brown et al. | |
| 5,073,782 A | 12/1991 | Huguenin et al. | |
| 5,126,677 A | 6/1992 | Campbell et al. | |
| 5,191,343 A | 3/1993 | Danzer et al. | |
| 5,218,294 A | 6/1993 | Soiferman | |
| 5,227,800 A | 7/1993 | Huguenin et al. | |
| 5,251,144 A | 10/1993 | Ramamurthi | |
| 5,270,222 A | 12/1993 | Moslehi | |
| 5,293,216 A | 3/1994 | Moslehi | |
| 5,300,879 A | 4/1994 | Masuda et al. | |
| 5,302,830 A | 4/1994 | Shivanandan | |
| 5,339,080 A | 8/1994 | Steinway et al. | |
| 5,406,209 A | 4/1995 | Johnson et al. | |
| 5,417,494 A | 5/1995 | Kempa et al. | |
| 5,424,633 A | 6/1995 | Soiferman | |
| 5,428,556 A | 6/1995 | Torizawa et al. | |
| 5,517,110 A | 5/1996 | Soiferman | |
| 5,537,909 A | 7/1996 | Schneider et al. | |
| 5,539,325 A | 7/1996 | Rostoker et al. | |
| 5,548,217 A | 8/1996 | Gibson et al. | |
| 5,552,705 A | 9/1996 | Keller | |
| 5,563,702 A | 10/1996 | Emery et al. | |
| 5,578,930 A | 11/1996 | Sheen | |
| 5,592,170 A | 1/1997 | Price et al. | |
| 5,610,705 A | 3/1997 | Brosnan et al. | |
| 5,631,572 A | 5/1997 | Sheen et al. | |
| 5,668,342 A | 9/1997 | Discher | |
| 5,714,888 A | 2/1998 | Naujoks | |
| 5,719,495 A | 2/1998 | Moslehi | |
| 5,723,055 A * | 3/1998 | Janssen | B22D 41/58 |
| | | | 222/603 |
| 5,754,450 A | 5/1998 | Solomon et al. | |
| 5,764,087 A | 6/1998 | Clark | |
| 5,798,577 A | 8/1998 | Lesesky et al. | |
| 5,824,271 A * | 10/1998 | Frank | G01N 27/12 |
| | | | 422/98 |
| 5,854,994 A | 12/1998 | Canada et al. | |
| 5,900,618 A | 5/1999 | Anlage et al. | |
| 5,900,833 A | 5/1999 | Sunlin et al. | |
| 5,905,572 A | 5/1999 | Li | |
| 5,905,577 A | 5/1999 | Wilsher et al. | |
| 5,907,491 A | 5/1999 | Canada et al. | |
| 5,859,596 A | 6/1999 | McRae | |
| 5,859,613 A | 6/1999 | Otto | |
| 5,942,991 A | 8/1999 | Gaudreau et al. | |
| 5,949,237 A * | 9/1999 | Berger | H01P 7/04 |
| | | | 324/634 |
| 6,049,220 A | 4/2000 | Borden et al. | |
| 6,049,301 A | 4/2000 | Weagant | |
| 6,057,765 A | 5/2000 | Jones et al. | |
| 6,118,279 A | 9/2000 | Field et al. | |
| 6,124,725 A | 9/2000 | Sato | |
| 6,137,439 A | 10/2000 | Bradford et al. | |
| 6,144,341 A | 11/2000 | Kraz | |
| 6,150,793 A | 11/2000 | Lesesky et al. | |
| 6,150,809 A | 11/2000 | Tiernan et al. | |
| 6,163,259 A | 12/2000 | Barsumian et al. | |
| 6,210,464 B1 * | 4/2001 | Nakanishi | B01D 53/22 |
| | | | 95/52 |
| 6,236,223 B1 | 5/2001 | Brady et al. | |
| 6,243,036 B1 | 6/2001 | Chadwick et al. | |
| 6,255,808 B1 * | 7/2001 | Hucker | G01R 31/1254 |
| | | | 250/206.1 |
| 6,268,738 B1 | 7/2001 | Gunthorpe et al. | |
| 6,281,697 B1 | 8/2001 | Masuda et al. | |
| 6,324,486 B1 | 11/2001 | Crook et al. | |
| 6,331,782 B1 | 12/2001 | White et al. | |
| 6,359,444 B1 | 3/2002 | Grimes | |
| 6,359,582 B1 | 3/2002 | MacAleese et al. | |
| 6,363,332 B1 | 3/2002 | Rangarajan et al. | |
| 6,375,347 B1 | 4/2002 | Bruce et al. | |
| 6,417,797 B1 | 7/2002 | Cousins et al. | |
| 6,455,766 B1 | 9/2002 | Cook et al. | |
| 6,456,070 B1 | 9/2002 | Kazama et al. | |
| 6,466,882 B1 | 10/2002 | Kang et al. | |
| 6,480,141 B1 | 11/2002 | Toth et al. | |
| 6,489,884 B1 | 12/2002 | Lamberson et al. | |
| 6,489,919 B1 | 12/2002 | Brock | |
| 6,496,703 B1 | 12/2002 | da Silva | |
| 6,612,172 B2 | 9/2003 | Cadet et al. | |
| 6,667,711 B1 | 12/2003 | Joshi et al. | |
| 6,700,526 B2 | 3/2004 | Witten | |
| 6,720,905 B2 | 4/2004 | Levitan et al. | |
| 6,759,850 B2 | 7/2004 | Harzanu et al. | |
| 6,759,863 B2 | 7/2004 | Moore | |
| 6,759,864 B2 | 7/2004 | Patel | |
| 6,765,527 B2 | 7/2004 | Jablonski et al. | |
| 6,785,553 B2 | 8/2004 | Chang et al. | |
| 6,825,456 B2 | 11/2004 | Chadwick et al. | |
| 6,859,285 B1 | 2/2005 | Chang | |
| 6,864,825 B2 | 3/2005 | Holly | |
| 6,870,889 B1 | 3/2005 | Sugiura | |
| 6,879,167 B2 | 4/2005 | Ju et al. | |
| 6,897,777 B2 | 5/2005 | Holmes et al. | |
| 6,927,579 B2 | 8/2005 | Blades | |
| 6,940,295 B2 | 9/2005 | Engelbart et al. | |
| 6,947,800 B2 | 9/2005 | Flanagan et al. | |
| 6,970,762 B1 | 11/2005 | Elliott et al. | |
| 6,985,771 B2 | 1/2006 | Fischell et al. | |
| 7,002,470 B1 | 2/2006 | Miao | |
| 7,010,386 B2 | 3/2006 | McDonnell et al. | |
| 7,034,660 B2 | 4/2006 | Watters et al. | |
| 7,039,491 B1 | 5/2006 | Delbrugge, Jr. et al. | |
| 7,046,187 B2 | 5/2006 | Fullerton et al. | |
| 7,086,593 B2 | 8/2006 | Woodard et al. | |
| 7,103,460 B1 | 9/2006 | Breed | |
| 7,130,624 B1 | 10/2006 | Jackson et al. | |
| 7,138,963 B2 | 11/2006 | Duff et al. | |
| 7,142,147 B2 | 11/2006 | Holly | |
| 7,145,356 B2 | 12/2006 | Sang Gi | |
| 7,145,453 B2 | 12/2006 | Miller, Jr. et al. | |
| 7,162,285 B2 | 1/2007 | Owens et al. | |
| 7,188,037 B2 | 3/2007 | Hidehira | |
| 7,218,093 B2 | 5/2007 | Cirkel et al. | |
| 7,220,990 B2 | 5/2007 | Aghababazadeh et al. | |
| 7,233,285 B2 | 6/2007 | Struckman | |
| 7,250,781 B2 | 7/2007 | Nakagawa et al. | |
| 7,250,785 B2 | 7/2007 | Kawaike et al. | |
| 7,256,055 B2 | 8/2007 | Aghababazadeh et al. | |
| 7,268,728 B1 | 9/2007 | Struckman | |
| 7,289,873 B2 | 10/2007 | Redecker et al. | |
| 7,328,126 B2 | 2/2008 | Chamness | |
| 7,355,417 B1 | 4/2008 | Shusterman et al. | |
| 7,391,356 B2 | 6/2008 | Brumley, II et al. | |
| 7,397,421 B2 | 7/2008 | Smith | |
| 7,424,338 B1 | 9/2008 | Wipert | |
| 7,427,947 B1 | 9/2008 | Dark et al. | |
| 7,454,202 B2 | 11/2008 | de La Chapelle | |
| 7,464,005 B1 | 12/2008 | Beetner et al. | |

(56) References Cited

U.S. PATENT DOCUMENTS

| | | |
|---|---|---|
| 7,466,157 B2 | 12/2008 | Miller |
| 7,492,303 B1 | 2/2009 | Levitan et al. |
| 7,512,511 B1 | 3/2009 | Schultz et al. |
| 7,515,094 B2 | 4/2009 | Keller, III |
| 7,554,352 B2 | 6/2009 | Huie |
| 7,609,199 B2 | 10/2009 | Nishijima et al. |
| 7,639,178 B1 | 12/2009 | Mulbrook et al. |
| 7,645,982 B1 | 1/2010 | King |
| 7,646,005 B2 | 1/2010 | Chase et al. |
| 7,671,784 B2 | 3/2010 | Steinway et al. |
| 7,683,830 B2 | 3/2010 | Montgomery et al. |
| 7,688,264 B2 | 3/2010 | Chun |
| 7,710,131 B1 | 5/2010 | Tiernan |
| 7,710,287 B2 | 5/2010 | Lange et al. |
| 7,777,671 B2 | 8/2010 | Schnitzer et al. |
| 7,777,672 B2 | 8/2010 | Schnitzer et al. |
| 7,778,367 B1 | 8/2010 | Stockmaster |
| 7,782,251 B2 | 8/2010 | Bishop et al. |
| 7,795,596 B2 | 9/2010 | Chowdhury |
| 7,844,341 B2 | 11/2010 | Von Arx et al. |
| 7,853,437 B2 | 12/2010 | Seguin et al. |
| 7,855,081 B2 | 12/2010 | Lueck et al. |
| 7,864,107 B1 | 1/2011 | Lehtola |
| 7,902,834 B2 | 3/2011 | Wolfe et al. |
| 7,928,577 B2 | 4/2011 | Sandhu et al. |
| 7,956,617 B1 | 6/2011 | McCarthy et al. |
| 7,999,723 B2 | 8/2011 | Jung et al. |
| 8,028,208 B2 | 9/2011 | Moore |
| 8,063,739 B2 | 11/2011 | Kean |
| 8,063,813 B1 | 11/2011 | Keller |
| 8,069,490 B2 | 11/2011 | Gross et al. |
| 8,103,463 B2 | 1/2012 | Kalgren et al. |
| 8,131,564 B2 | 3/2012 | Dicks et al. |
| 8,193,819 B2 | 6/2012 | Wang et al. |
| 8,294,616 B1 | 10/2012 | Ormesher et al. |
| 8,344,745 B2 | 1/2013 | Aghababazadeh et al. |
| 8,390,307 B2 | 3/2013 | Slupsky et al. |
| 8,537,050 B2 | 9/2013 | Freeman et al. |
| 8,548,649 B2 | 10/2013 | Guyette et al. |
| 8,643,539 B2 | 2/2014 | Pauly et al. |
| 8,661,980 B1 | 3/2014 | Roemerman et al. |
| 8,825,823 B2 | 9/2014 | Keller, III |
| 8,878,725 B2 | 11/2014 | Lu |
| 9,059,189 B2 | 6/2015 | Keller, III et al. |
| 9,205,270 B2 | 12/2015 | Pathak et al. |
| 9,285,463 B1 | 3/2016 | Freeman et al. |
| 9,443,843 B2 | 9/2016 | Lee et al. |
| 9,448,186 B2 | 9/2016 | Marchetti |
| 9,494,512 B2 | 11/2016 | Wu et al. |
| 2001/0011903 A1 | 8/2001 | O'Neill et al. |
| 2001/0056340 A1 | 12/2001 | Gorin et al. |
| 2002/0011852 A1 | 1/2002 | Mandelis et al. |
| 2002/0024432 A1 | 2/2002 | Lin et al. |
| 2002/0039030 A1 | 4/2002 | Khazei |
| 2002/0075017 A1 | 6/2002 | Edwards et al. |
| 2002/0121915 A1 | 9/2002 | Alonso Montull et al. |
| 2003/0001596 A1 | 1/2003 | Suga et al. |
| 2003/0034444 A1 | 2/2003 | Chadwick et al. |
| 2003/0071262 A1 | 4/2003 | Weiner et al. |
| 2003/0137318 A1 | 7/2003 | Enachescu et al. |
| 2003/0155927 A1 | 8/2003 | Pinto et al. |
| 2003/0179126 A1 | 9/2003 | Jablonski et al. |
| 2003/0206027 A1 | 11/2003 | Nozoe et al. |
| 2004/0027149 A1 | 2/2004 | Aitren et al. |
| 2004/0041724 A1 | 3/2004 | Levitan et al. |
| 2004/0058343 A1 | 3/2004 | MacDonald |
| 2004/0078160 A1 | 4/2004 | Frei et al. |
| 2004/0095243 A1 | 5/2004 | Holmes et al. |
| 2004/0100280 A1 | 5/2004 | Ju et al. |
| 2004/0218249 A1 | 11/2004 | Kochergin |
| 2004/0254457 A1 | 12/2004 | van der Weide |
| 2005/0039743 A1* | 2/2005 | Taylor ............ A61M 15/0045 128/203.15 |
| 2005/0046430 A1 | 3/2005 | Kinnunen et al. |
| 2005/0064922 A1 | 3/2005 | Owens et al. |
| 2005/0116307 A1 | 6/2005 | De Jongh et al. |
| 2005/0165456 A1 | 7/2005 | Mann et al. |
| 2005/0265124 A1 | 12/2005 | Smith |
| 2006/0058606 A1 | 3/2006 | Davis et al. |
| 2006/0082488 A1 | 4/2006 | Keller, III |
| 2006/0103378 A1 | 5/2006 | Pakdaman et al. |
| 2006/0114157 A1 | 6/2006 | Kolanek et al. |
| 2006/0152232 A1 | 7/2006 | Shvets et al. |
| 2006/0208672 A1 | 9/2006 | Achenbach et al. |
| 2006/0220858 A1 | 10/2006 | Kawamata |
| 2006/0259082 A1 | 11/2006 | Youker et al. |
| 2007/0013577 A1 | 1/2007 | Schnitzer et al. |
| 2007/0027643 A1 | 1/2007 | Lesesky et al. |
| 2007/0040118 A1 | 2/2007 | Cheng et al. |
| 2007/0046298 A1 | 3/2007 | Safai et al. |
| 2007/0063886 A1 | 3/2007 | Brumley, II et al. |
| 2007/0069949 A1 | 3/2007 | Ferreol et al. |
| 2007/0120571 A1 | 5/2007 | Huie |
| 2007/0120738 A1 | 5/2007 | Stroud |
| 2007/0139247 A1 | 6/2007 | Brown et al. |
| 2007/0213951 A1 | 9/2007 | Van Eeden |
| 2007/0214133 A1 | 9/2007 | Liberty et al. |
| 2007/0229270 A1 | 10/2007 | Rofougaran |
| 2007/0234058 A1 | 10/2007 | White |
| 2007/0279071 A1 | 12/2007 | Orton |
| 2007/0282541 A1 | 12/2007 | Griess et al. |
| 2008/0012579 A1 | 1/2008 | Kuhns et al. |
| 2008/0048673 A1 | 2/2008 | Tan et al. |
| 2008/0094273 A1 | 4/2008 | Doyen |
| 2008/0103555 A1 | 5/2008 | Dicks et al. |
| 2008/0141072 A1 | 6/2008 | Kalgren et al. |
| 2008/0168895 A1 | 7/2008 | Duong |
| 2008/0169968 A1 | 7/2008 | Easthope et al. |
| 2008/0177486 A1 | 7/2008 | Farkas |
| 2008/0204275 A1 | 8/2008 | Wavering et al. |
| 2008/0206718 A1 | 8/2008 | Jaklitsch et al. |
| 2008/0254738 A1 | 10/2008 | Brumley et al. |
| 2008/0259084 A1 | 10/2008 | Chang et al. |
| 2008/0281196 A1 | 11/2008 | Sornes |
| 2008/0284609 A1 | 11/2008 | Rofougaran |
| 2008/0297396 A1 | 12/2008 | Dark et al. |
| 2009/0002000 A1 | 1/2009 | Nikawa |
| 2009/0030487 A1 | 1/2009 | Lang |
| 2009/0078146 A1 | 3/2009 | Tepera et al. |
| 2009/0099830 A1 | 4/2009 | Gross et al. |
| 2009/0154589 A1 | 6/2009 | Monnerie |
| 2009/0216498 A1 | 8/2009 | Seguin et al. |
| 2009/0218657 A1 | 9/2009 | Rofougaran |
| 2009/0243924 A1 | 10/2009 | Twitchell, Jr. et al. |
| 2009/0306920 A1 | 12/2009 | Zwinger et al. |
| 2009/0322585 A1 | 12/2009 | Galasso |
| 2010/0033386 A1 | 2/2010 | Lewis et al. |
| 2010/0035557 A1 | 2/2010 | Shellhammer |
| 2010/0039340 A1 | 2/2010 | Brown |
| 2010/0073229 A1 | 3/2010 | Pattabiraman et al. |
| 2010/0073665 A1 | 3/2010 | Zhao et al. |
| 2010/0097269 A1 | 4/2010 | Loidl et al. |
| 2010/0114216 A1 | 5/2010 | Krause et al. |
| 2010/0123453 A1 | 5/2010 | Pauly et al. |
| 2010/0125438 A1 | 5/2010 | Audet |
| 2010/0171446 A1 | 7/2010 | Retsky |
| 2010/0182189 A1 | 7/2010 | Jung et al. |
| 2010/0237854 A1 | 9/2010 | Kumhyr et al. |
| 2010/0241864 A1 | 9/2010 | Kelley et al. |
| 2010/0289686 A1 | 11/2010 | Jung et al. |
| 2010/0295552 A1 | 11/2010 | Li et al. |
| 2010/0315295 A1 | 12/2010 | Tucek et al. |
| 2010/0332199 A1 | 12/2010 | Dhanekula et al. |
| 2011/0068818 A1 | 3/2011 | Fukami |
| 2011/0095934 A1 | 4/2011 | Freeman et al. |
| 2011/0210829 A1 | 9/2011 | Kean |
| 2011/0235742 A1 | 9/2011 | London et al. |
| 2011/0270337 A1 | 11/2011 | Doerr et al. |
| 2011/0313651 A1 | 12/2011 | Hyde et al. |
| 2011/0320170 A1 | 12/2011 | Pathak et al. |
| 2012/0007982 A1 | 1/2012 | Giuffrida et al. |
| 2012/0154213 A1 | 6/2012 | Bull et al. |
| 2012/0165693 A1* | 6/2012 | Williams ............ A61B 5/082 600/532 |

(56) References Cited

U.S. PATENT DOCUMENTS

| | | |
|---|---|---|
| 2012/0179812 A1 | 7/2012 | Keller, III |
| 2012/0223403 A1 | 9/2012 | Keller, III et al. |
| 2012/0226463 A1 | 9/2012 | Keller, III et al. |
| 2012/0305773 A1 | 12/2012 | Wu et al. |
| 2013/0050010 A1 | 2/2013 | Nordlander |
| 2013/0082717 A1 | 4/2013 | Kim et al. |
| 2013/0137066 A1 | 5/2013 | Pollak et al. |
| 2013/0229310 A1 | 9/2013 | Parks et al. |
| 2013/0328710 A1 | 12/2013 | Keller, III |
| 2014/0043184 A1 | 2/2014 | Malaga |
| 2014/0218229 A1 | 8/2014 | Pauly et al. |
| 2014/0278214 A1 | 9/2014 | Broad et al. |
| 2014/0313071 A1 | 10/2014 | Mccorkle |
| 2014/0347074 A1 | 11/2014 | Nadeau |
| 2015/0009073 A1 | 1/2015 | Keller, III |
| 2015/0137830 A1 | 5/2015 | Keller, III et al. |

FOREIGN PATENT DOCUMENTS

| | | |
|---|---|---|
| JP | 63085373 | 4/1988 |
| JP | 06011530 | 1/1994 |
| JP | H11174130 | 7/1999 |
| JP | 2000076387 | 3/2000 |
| JP | 2003503679 | 1/2003 |
| JP | 2004245709 | 9/2004 |
| JP | 2011174709 | 9/2011 |
| JP | 2012026913 | 2/2012 |
| KR | 20090092515 | 9/2009 |
| KR | 101077441 | 10/2011 |
| WO | 2009047585 | 4/2009 |
| WO | 2015134148 | 9/2015 |

OTHER PUBLICATIONS

William E. Cobb et al; Intrinsic Physical-Layer Authentication of Integrated Circuits; IEEE Transactions on Information Forensics and Security, vol. 7, No. 1 Feb. 2012.

Y.P. Zhang, Duixian Liu; Antenna-on-Chip and Antenna-in-Package Solutions to Highly Integrated Millimeter-Wave Devices for Wireless Communications, 2009, vol. 57 No. 10.

Walter J. Keller and Bogdan Pathak; Advanced Detection of Electronic Counterfeits; Apr. 19, 2013; Nokomis, Inc.

John H. Marburger, III; Research Challenges in Combating Terrorist Use of Explosives in the United States; Subcommittee on Domestic Improvised Explosive Devices; Dec. 2008.

U.S. Department of Justice; Enhanced Tools for Improvised Explosive Devices (IED) and Vehicle Borne IED Defeat; Oct. 2005.

* cited by examiner

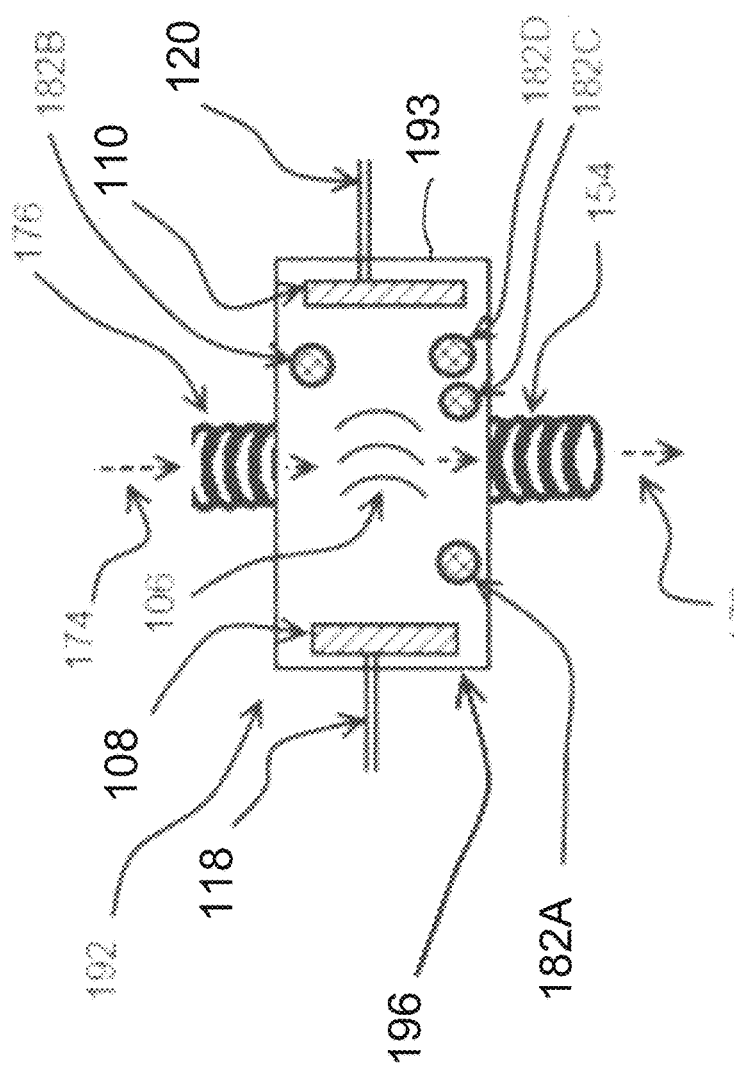

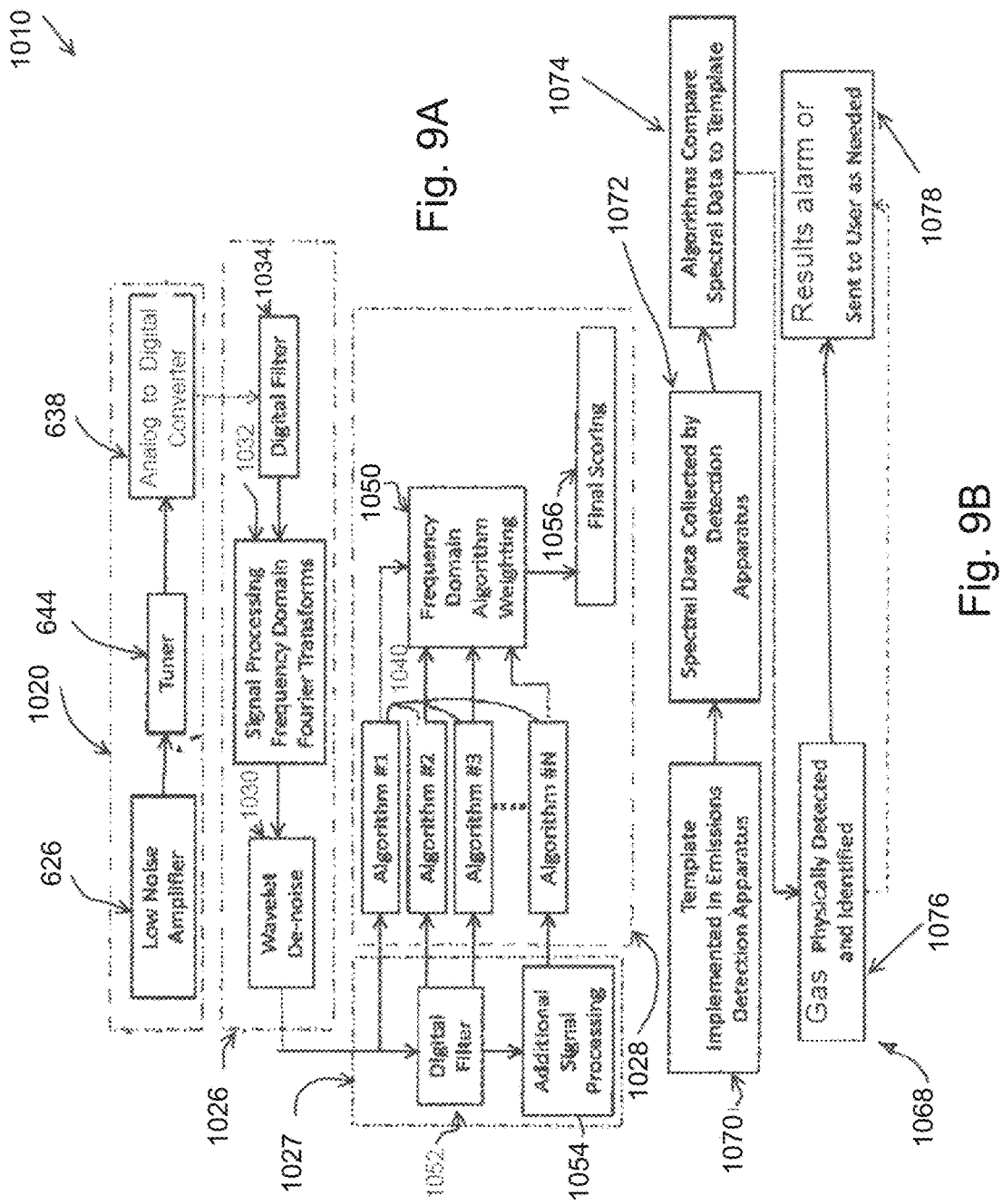

APPARATUS AND METHOD TO IDENTIFY AND MEASURE GAS CONCENTRATIONS

CROSS-REFERENCE TO RELATED APPLICATIONS

The present application claims priority to and is a non-provisional of a provisional U.S. patent application No. 62/463,126 tilted "Device and Method to Measure Gas Concentrations using Electromagnetic Techniques" and filed on Feb. 24, 2017 by Applicant Nokomis, Inc. The present application also relates to co-pending U.S. patent application Ser. No. 14/459,717, titled "Device and Method to Detect, Analyze or Measure Tissue Characteristics and Anomalies using Electromagnetic Techniques" and filed concurrently herewith by Applicant Nokomis, Inc. The foregoing references are hereby incorporated herein by reference in their entirety.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND

1. Technical Field

The subject matter relates to a gas or chemical concentration identification and/or measurement. It further relates to identifying, detecting, measuring and/or analyzing gas or chemical concentrations using emissions of electrical or electromagnetic energy modified or influenced by gases. It further relates to analyzing spectra of gasses. It additionally relates to analyzing spectra of gasses particularly but not limited to those from human breath.

2. Description of Related Art

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Conventionally employed diagnosis of Pulmonary Oxygen Toxicity, PO2T, is difficult due to the commonality of clinical symptoms, such as visual disturbance, ear problems, dizziness, confusion, and nausea may be attributed with many other physical ailments. These conventionally employed solutions can typically be subjective and difficult to diagnose in conditions that are conducive to PO2T. The conventional solution further may require self-diagnosis in the absence of trained personnel in the conditions that are conducive to PO2T. Conventionally employed methods analyze visual acuity, ear problems, dizziness, confusion, and nausea, and are limited in these operating conditions.

Other conditions, such as heart failure and pneumonia, also have similar clinical symptoms such as fluid buildup in the lungs, shortness of breath, and fatigue. Heart failure has several laboratory based measurements that may be made, but there is no definitive diagnostic for pneumonia.

The above described solutions typically do not provide an objective numerical evaluation of blood oxygen levels or damage to the heart or lungs. Further, the above described solutions typically require a skilled evaluator and a learning period for the evaluator. These methods are not amenable to automation, nor to electronic transmission of analysis results, and have the potential for misinterpretation of clinical examinations.

Conventional use of RF signals for the detection of gas(ses) has been limited to systems that use more than two antennas, are confined to specific frequency regions, require high RF energy above human exposure limits, are not performed at atmospheric pressure, or use multiple RF signals to identify spectral regions. Other conventional uses that have embodiments of RF sensors with thermistors require the thermistor for signal calibration. Further, the above solutions do not address the ability to measure gas(ses) of interest specifically for the purposes of health diagnostics in humans.

Conventional RF chemical sensors rely on the combination of inputs, in the form of multiple RF measurements, or RF measurements combined with temperature measurements, for accurate calibration of gas(ses) concentration(s). These methods are not able to accurately detect and/or measure gas(ses) of interest without supplementary sensor input.

Furthermore, conventional methods to diagnose human health conditions have been limited to electrochemical sensors, chemical sensors, trained physicians, X-ray, magnetic resonance, radio tomography, IR imaging, and nanotechnology. Most of these methods must be performed in a clinical setting, or by skilled evaluators. The sensors that are amiable to automation have high specificity to the desired test, and are not readily adaptable.

BRIEF DESCRIPTION OF THE DRAWINGS

The accompanying drawings are incorporated in and constitute part of the specification and illustrate various embodiments. In the drawings:

FIG. 1C illustrates an exemplary device to identify and measure gas or chemical concentrations;

FIGS. 9A-9B illustrate exemplary embodiments of software and hardware architecture/operation.

LIST OF REFERENCE NUMERALS

Figure 1A:
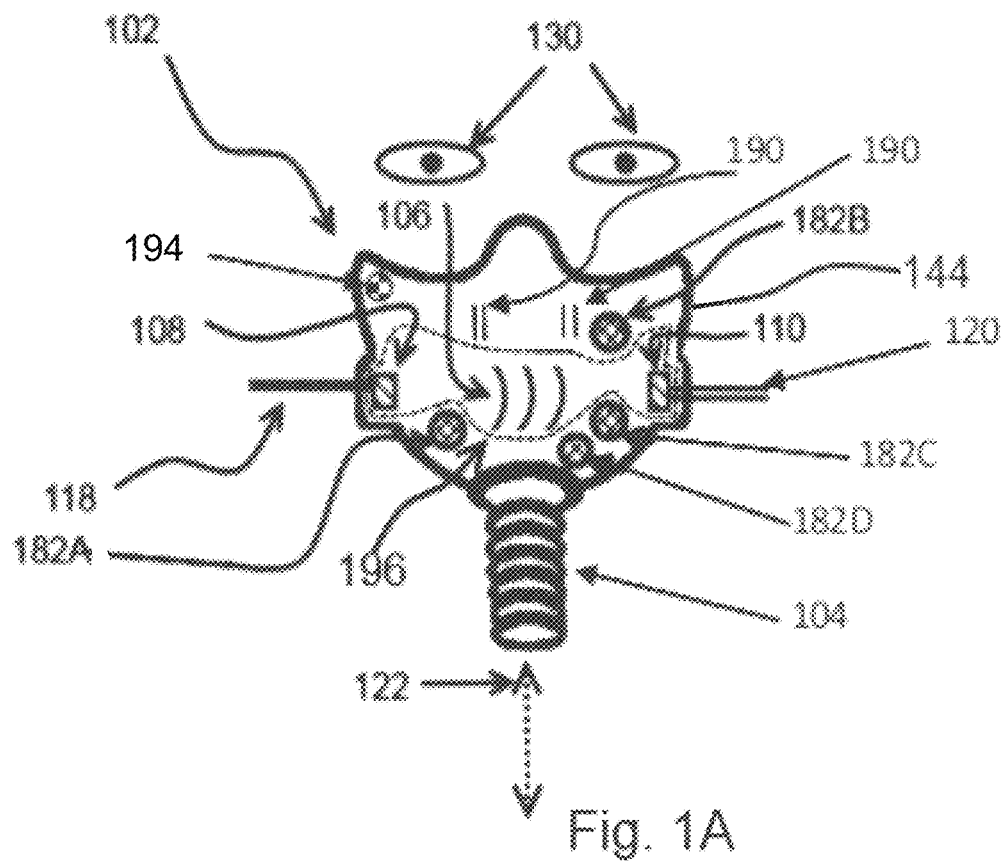
FIG. 1A illustrates a front view of an exemplary device to identify and measure gas or chemical concentrations.

102—Device/Mask
104—Air Intake/Evacuation Member
106—Electromagnetic Energy Emission
108—Transmit Antenna
110—Receive Antenna
118—Input/Output (I/O) Coaxial Cable(s)
120—Input/Output (I/O) Coaxial Cable(s)
122—Air Intake/Ventilation
130—Person
144—Member of the Device
150—Side exploded view of FIG. 1A showing Faraday cage containing gas to be measured
154—Evacuation Member
108—Transmit Antenna
172—Gas flow evacuation
174—Gas flow Supply
176—Intake Member
182A—Thermistor (Optional)
182B—Solid State Partial Pressure Sensor (Optional)
182C—Solid State Partial Pressure Sensor (Optional)
182D—Solid State Partial Pressure Sensor (Optional)
190—Air Intake/Evacuation Member
192—Gas Measurement Device
193—Enclosure
194—Microphone (Optional)
196—Faraday Cage
200—Software Entity
202—Code for Gas Measurement acquisition execution
204—Code for Calculation to Convert Absorption Amplitude to Concentration
206—Electrical signal from Partial Pressure Sensors
208—Temperature signal from Thermistor
210—Source Code Calculation to Convert Partial Pressure(s) and Temperature to Concentration
212—Source Code Analysis of Concentrations
214—Outcome of Concentration Analysis for Criteria of Normal Concentrations
216—Outcome of Concentration Analysis for Criteria of Dangerous Concentrations
302—Device
303—Printed Circuit Board (PCB)
304—Input/Output (I/O) Cable(s)
305—PCB
320—Oxygen Gas
322—Nitrogen Gas
324—Carbon Dioxide Gas
352—Device
354—Input/Output (I/O) Cable(s)
356—Wire(s)
360—PCB
400—Exemplary method to Create a RF Reflection and/or Absorption (typically Frequency and dB) Signature for Gas(es) Through Simulation
402—Modeling Chemical Properties for Gas(es) of Interest
404—Identification of RF Absorption and/or Reflection Spectral Regions
406—Creation of Signatures for Chemical Identification and/or Quantification
450—Exemplary method to Create a RF Reflection and/or Absorption Signature for Gas(es) Through Experimentation
452—Frequency Region to Experimentally Evaluate the Chemical(s) Over
454—Set Initial Test Frequency
456—Transmission of Electromagnetic Waves through Gas(es) of Interest
458—Measurement of Electromagnetic Waves after Interacting with the Chemical(s) of Interest
460—Increment Test Frequency
462—Frequencies of significance above noise floor are Identified Developing a Verification Signature
464—Develop a Verification Signature
500—Hardware Components of Control System
502—Control for the Generation of Frequency of the Transmitted Electromagnetic Wave
504—Control for Amplifying, Impedance Matching, and/or Acquiring Electromagnetic Energy
510—Means of Preparing Captured Electromagnetic Energy
512—Means for Converting Captured Electromagnetic Signal into a Digital Signature
514—Means for Processing and Analyzing Captured Signal
516—Software Control System and GUI
541—Convey RF energy from RF preparation Hardware component 504 to devices 102 or 192
552—Control System and GUI Hardware containing the Apparatus Software
561—Receive Signal
582—Chemical(s) of Interest
586—Modified/Influenced Electromagnetic energy
602—General Purpose Processor(s)
604—Digital Signal Processing Integrated Circuit(s) (Optional)
606—Programmable Logic (optional)
620A—Apparatus to Perform Conversions to and/or from Time Domain Data to Frequency Domain Data
622—GUI Display and/or Alarm
626—Low Noise Amplifier(s)
632—Optional Directional Coupler(s)
634—Radio Frequency Power Amplifier(s)
636—Illumination Frequency Source
638—Analog to Digital Converter(s)
644—Radio Frequency Tuner(s)
650—Block Diagram of Apparatus to Detect and/or Characterize and/or Quantify Chemical(s) of Interest
680—Electromagnetic energy spectrum reflected from chemical or gas of interest
687—Filter Setting(s) (Bandpass, highpass, lowpass, notch, and/or other filters to eliminate unwanted signals)
692—Single Board Computer(s)
700—Absorbed Energy of Isopropyl Alcohol, Formaldehyde, and Acetone
702—Absorbed Energy Region of Interest of Isopropyl Alcohol
704—Absorbed Energy Region of Interest of Formaldehyde
706—Absorbed Energy Region of Interest of Formaldehyde
708—Absorbed Energy Region of Interest of Acetone
802—Radio Frequency Absorption Features of Propanol from a Span of 8 to 18 GHz
804—Radio Frequency Absorption Features of Propanol from a Span of 10.6 to 11.6 GHz
806—Non-Inclusive List of Radio Frequency Characterized Chemicals 1010—Gas Concentration Determination/Estimation Apparatus/Process
1020—Analog signal circuitry
1026—Frequency Domain Transform
1027—Digital Filter and Processing
1028—Algorithmic Assessment of Signal
1030—Wavelet De-noising
1032—Signal Processing Fourier Transform
1034—Digital Filter
1040—Embedded Algorithms
1050—Frequency Domain Algorithm Weighting Calculation
1052—Digital Filter
1054—Signal Processing
1056—Final Scoring
1068—Gas Concentration Determination/Estimation Process
1070—Embedded Gas Signal Template
1072—Collected Spectral Data
1074—Algorithm Comparison
1076—Gas(ses) Detected
1078—Results Alarm

DETAILED DESCRIPTION OF EXEMPLARY EMBODIMENTS

Prior to proceeding to the more detailed description of the present subject matter, it should be noted that, for the sake of clarity and understanding, identical components which have identical functions have been identified with identical reference numerals throughout the several views illustrated in the drawing figures.

The following detailed description is merely exemplary in nature and is not intended to limit the described examples or the application and uses of the described examples. As used herein, the words "example", "exemplary" or "illustrative" means "serving as an example, instance, or illustration." Any implementation described herein as "example", "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims.

The term "or" when used in this specification and the appended claims is not meant to be exclusive; rather the term is inclusive, meaning either or both.

The term "couple" or "coupled" when used in this specification and appended claims refers to an indirect or direct physical connection between the identified elements, components, or objects. Often the manner of the coupling will be related specifically to the manner in which the two coupled elements interact.

The term "directly coupled" or "coupled directly," when used in this specification and appended claims, refers to a physical connection between identified elements, components, or objects, in which no other element, component, or object resides between those identified as being directly coupled.

The term "operatively coupled," when used in this specification and appended claims, refers to a physical connection between identified elements, components, or objects, wherein operation of one of the identified elements, components, or objects, results in operation of another of the identified elements, components, or objects.

It is to be understood that the singular forms "a," "an," and "the" include plural referents unless the context clearly dictates otherwise. Thus, for example, reference to "a circuit" includes reference to one or more of such circuits.

It is to be understood that electromagnetic emissions may be, but is not limited to radio frequency (RF) emissions, microwave emissions, millimeter wave emissions and terahertz wave emissions.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

Furthermore, there is no intention to be bound by any expressed or implied theory presented in the preceding technical field, background, or the following detailed description. It is also to be understood that the specific devices and processes illustrated in the attached drawings, and described in the following specification, are simply examples of the inventive concepts defined in the appended claims. Hence, specific dimensions and other physical characteristics relating to the examples disclosed herein are not to be considered as limiting, unless the claims expressly state otherwise.

The particular embodiments of the present disclosure generally provide devices, apparatuses, and methods directed to identifying, detecting, measuring and/or analyzing gas or chemical concentrations using emissions of electrical or electromagnetic energy modified or influenced by such gases or chemicals.

In particular embodiments, gas or chemical concentrations are measured in a non-contact manner using microwave spectroscopy techniques.

In particular embodiments, the frequency ranges from over 100 Mhz to under 30 Ghz to enable lower cost and or portable electronic control members. In particular embodiments, the high frequency limit is 18 Ghz to enable even lower hardware costs.

In particular embodiments, a characterizing device comprises a set of antennas, one or more circuits disposed to provide electrical energy to antennas, one or more circuits disposed to receive electrical energy from antennas.

In particular embodiments, the characterizing device comprises a means for measuring electrical energy properties from said antennas, which are influenced by characteristic(s) of chemicals within the electrical influence of the antennas.

In particular embodiments, solid state partial pressure sensors are used to measure and determine absolute concentrations of oxygen, nitrogen, and/or carbon dioxide, as well as temperature, including a set of solid-state partial pressure sensors, one or more circuits disposed to provide electrical energy to sensors, one or more circuits disposed to receive electrical energy from sensors which are influenced by characteristics of chemical gasses within the measurement influence of the sensors.

In particular embodiments, the apparatus comprises two antennas, an active RF supply, the control software, low noise amplifiers, RF tuners, RF filters, analog to digital converters, programmable logic device(s), general purpose processor(s) and/or single board computer(s), optional GUI. The apparatus may comprise an optional directional coupler, an optional solid-state oxygen, nitrogen, or carbon dioxide sensors, optional thermistor, and/or optional alarm.

Now in reference to Figures, FIGS. 1-4 illustrate exemplary devices configured to subject a gas mixture, such as expirate 122 from a person 130, to emissions of electromagnetic energy or spectrum 106. In other words, the device 102 is also configured to influence emissions of electromagnetic energy or spectrum 106 by the expirate 122 from the person 130.

Figure 1B:
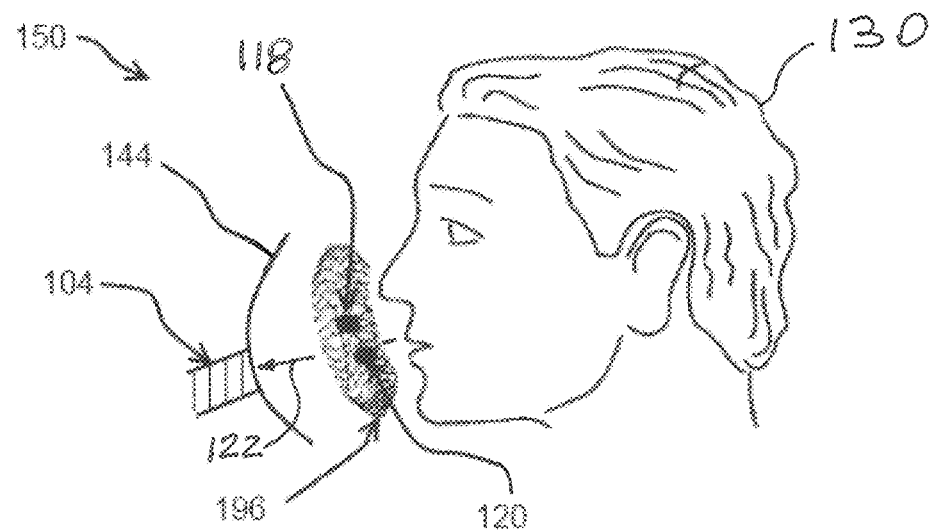
FIG. 1B illustrates a side view of the device of FIG. 1A.
Figure 6:
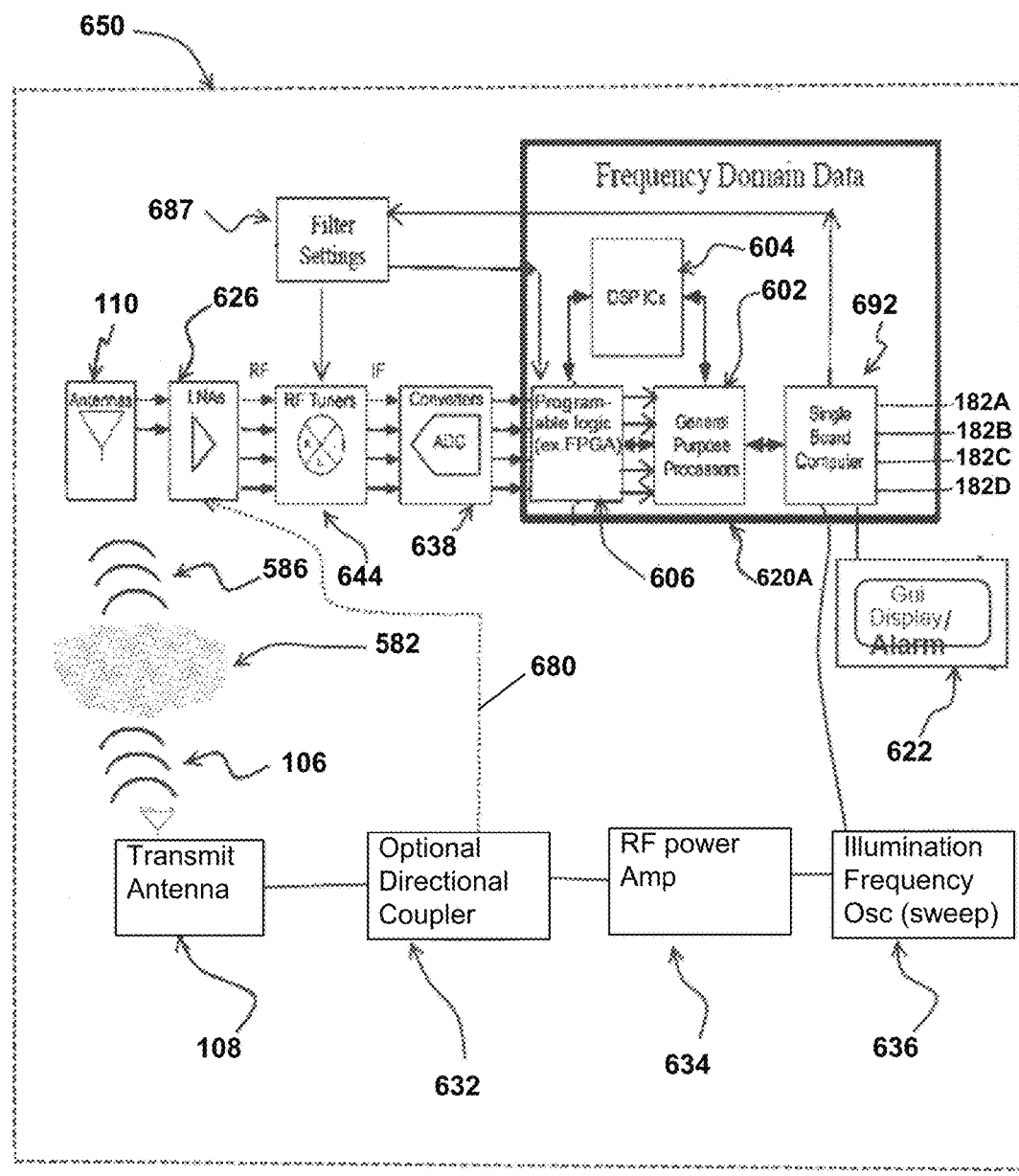
FIG. 6 illustrates an exemplary embodiment of a chemical gas detection and characterization hardware architecture.

In reference to FIGS. 1A-1B, therein is illustrated an exemplary device 102 that comprises a member 144 and a pair of antennas 108, 110 that are disposed near or on a surface of the member 144. The antennas 108 and 110 are spaced apart from each other across the width of the body of FIG. 1A. One of the antennas, for example such as a first antenna 108, is configured and operable as a transmit antenna to emit or transmit electromagnetic energy emission or spectrum 106. The electromagnetic energy emission or spectrum can be also referred to in this document as an electromagnetic field that is passed through expirate 122. Frequency or frequencies of the electromagnetic energy emission or spectrum 106 can be preselected based on a frequency or frequencies that the expirate 122 is most responsive to. The transmit antenna 108 can be also configured an operable to receive electromagnetic energy spectrum reflected from the expirate 122. The other or second antenna 110 is configured and operable as a receive antenna to receive an electromagnetic energy field/wave/spectrum difference between a transmitted electromagnetic energy emission or field/wave/spectrum 106 from the transmit antenna 108 and an electromagnetic energy emission or field/wave/spectrum being absorbed or reflected by expirate 122. The transmit antenna 108 is connected, by a cable 118, to source(s) configured to generate electromagnetic energy, for example such as illustrated in FIG. 6. The receive antenna 110 is connected, for example by way of a cable 120, to a device configured to process such received electromagnetic energy emission or field/wave/spectrum 106 received at the antenna 110. Such device can be a low noise amplifier of FIG. 6. Cables 118, 120 can be of a coaxial type. Furthermore, the cable 118 can be referred to as an input cable and cable 120 can be referred to as an output cable in relationship to the device 102. In a further reference to FIGS. 1A-1B, the device 102 can be configured in a form of a mask wearable by a person 130 or positioned next to the person 130 in a close proximity to the mouth of the person 130. In either form, the mask 102 is shaped and sized so that antennas 108 and 110 are positioned below the eyes and in a general alignment with the mouth of the person 130 so that the electromagnetic energy emission 106 passes through the expirate 122. As such, the receive antenna 110 receives transmitted electromagnetic energy emission or field/wave/spectrum 106 being influenced by the expirate 122. The exemplary electromagnetic energy emission 106 is in a radio frequency (RF) range. Thus, the receive antenna 110 outputs an RF signal representative of the received electromagnetic energy emission or field/wave/spectrum 106 influenced by the expirate 122.

The antennas 108 and 110 are illustrated as being aligned in a direction which is generally normal to a passage direction of the expirate 122. However, one of the antennas 108, 110 can be disposed at an angle in the plane of FIG. 1A to the other antenna. When one of the antennas disposed at an angle, additional signal corrections may be required.

The device 102 can further comprise an optional air intake/evacuation member. In an example, the air intake/evacuation member can be a hollow tubular member 104 that is coupled to the body 144 so as to either deliver air supply to the person 130 or facilitate exit or outlet of the expirate 122. The air intake/evacuation member 104 can be considered as a ventilation tube. In an example, the air intake/evacuation member can be at least one check valve 190 to allow air to flow only in one direction, for example as an inlet only. In an example, check valve 190 can be used in a combination with the ventilation tube 122 with the check valve 190 being configured as an air intake and ventilation tube 122 being configured as an air outlet. In an example, the check valve 190 can be used in a combination with the ventilation tube 122 with the check valve 190 being configured as an air outlet and the ventilation tube 122 being configured as the air inlet.

The device 102 can also comprise an optional Faraday Cage 196 configured to shield the receiver from external noise as well as to reduce human exposure to the microwave illumination energy. When Faraday Cage 196 is provided, both the receive antenna 110 and the transmit antenna 108 are encased by the Faraday Cage 196. In a mask embodiment of FIGS. 1A-1B, the Faraday cage 196 is typically of an electrically conductive screen type, not a solid metal shield, and allows expirate 122 to enter and exit the Faraday Cage 196 easily. It must be noted that the Faraday Cage 196 may be integrated with and/or into the antennas such as transmit and receive horn antennas, such that the horn forms part of the Faraday Cage 196.

The device 102 can be a mask worn by a user. The mask 102 can be any one of a medical mask, a mask used by divers, a mask used by pilots, an amusement-appearing mask worn by children at play, and the like.

In operation, the person 130 receives a supply of air either through the air intake/evacuation member 190 or the air intake/evacuation member 104. The device 102 can be configured so that the supply of air will pass through electromagnetic energy emission or field/wave/spectrum 106. The expirate 122 can be evacuated through either the air intake/evacuation member 190 or the air intake/evacuation member 104. The antennas 108, 110 can be operable to continuously or intermittently transmit/receive emissions of electromagnetic energy.

In reference to FIG. 1C, therein is illustrated an exemplary device 192 that comprises a body in a form of a hollow enclosure 193. The hollow enclosure 193 can be configured as an optional Faraday Cage 196, which can be constructed either as a solid metal shield type or as a wire mesh type. The device 192 also comprises a pair of antennas 108, 110. The antennas 108 and 110 are spaced apart from each other across the width of the body of FIG. 1C. One of the antennas, for example such as a first antenna 108, is configured and operable as a transmit antenna to emit or transmit electromagnetic energy emission or spectrum 106. The transmit antenna 108 can be also configured an operable to receive electromagnetic energy spectrum reflected from the expirate 122. The other or second antenna 110 is configured and operable as a receive antenna to receive an electromagnetic energy difference between a transmitted electromagnetic energy emission or spectrum 106 from the transmit antenna 108 and an electromagnetic energy emission spectrum being absorbed or reflected by expirate 122. The receive antenna 110 is connected, for example by way of a cable 120, to a device configured to process such received electromagnetic energy emission or field/wave/spectrum 106 received at the antenna 110. Cables 118, 110 can be of a coaxial type. Furthermore, the cable 108 can be referred to as an input cable and cable 110 can be referred to as an output cable in a relationship to the device 192.

The device 192 is considered to receive a gas flow 174 through the intake member 176 and outlet the gas flow as gas flow 172 through the outlet or evacuation member 154, after the gas flow 174 is influenced by the emissions or field/wave/spectrum 106. Each of the intake member 176 and outlet member 154 can be a hollow tube.

As such, the receive antenna 110 receives transmitted electromagnetic energy emission 106 being influenced by the gas flow. The exemplary electromagnetic energy emission 106 is in a radio frequency (RF) range. Thus, the receive antenna 110 outputs an RF signal representative of the received electromagnetic energy emission 106 influenced by the gas flow.

The antennas 108 and 110 are illustrated as being aligned in a direction which is generally normal to a passage direction of the gas flow 174. However, one of the antennas 108, 110 can be disposed at an angle in the plane of FIG. 1C to the other antenna. When one of the antennas disposed at an angle, additional signal corrections may be required. Although, antennas 108, 110 have been illustrated as being positioned within the enclosure 193, these antennas can be positioned external to the enclosure 193. When positioned external to the enclosure 193, the one or both of the antennas 108 and 110 can be mounted for a movement relative to the enclosure 193, for example with a robotic device (not shown).

In operation, the gas flow is received through the intake member 176 and is evacuated through the evacuation member 154 after passing through the electromagnetic energy emission 106. The antennas 108, 110 can be operable to continuously or intermittently transmit/receive electromagnetic energy emission 106. The antennas 108, 110 can be also moved, either manually or with a with the robotic device (not shown) when the antennas 108, 110 are mounted external to the enclosure 193.

In the embodiments of FIGS. 1A-1C, one or both of the devices 102 and 192 can be adapted with one or more of the optional sensors 182A, 182B, 182C and 182D. The sensor 182A can be of a thermistor type, outputting a voltage signal in a response to measuring temperature of the expirate 122, or evacuated gas flow 172. Sensors 182B, 182C and 182D can be of a partial pressure type, each outputting a voltage signal in a response to respectively measuring oxygen, nitrogen, and carbon dioxide levels in the expirate 122 or evacuated gas flow 172. The device 102 can be also adapted with an optional microphone 194 for communications between the person 130 and another person or external environment. The sensors 182A, 182B, 182C, and thermistor 182D can be mounted on an interior wall surface of the enclosure 193 and typically outside a possible screen-type Faraday cage 196. The sensors 182A, 182B, 182C, and thermistor 182D can be disposed in any relationship to each other.

Furthermore, in the embodiment of FIG. 1C, the person 130 can be any one of a subject, an operating device, a storage reservoir and the like, configured to communicate a gas flow or a gaseous mixture flow external thereto.

Figure 2A:
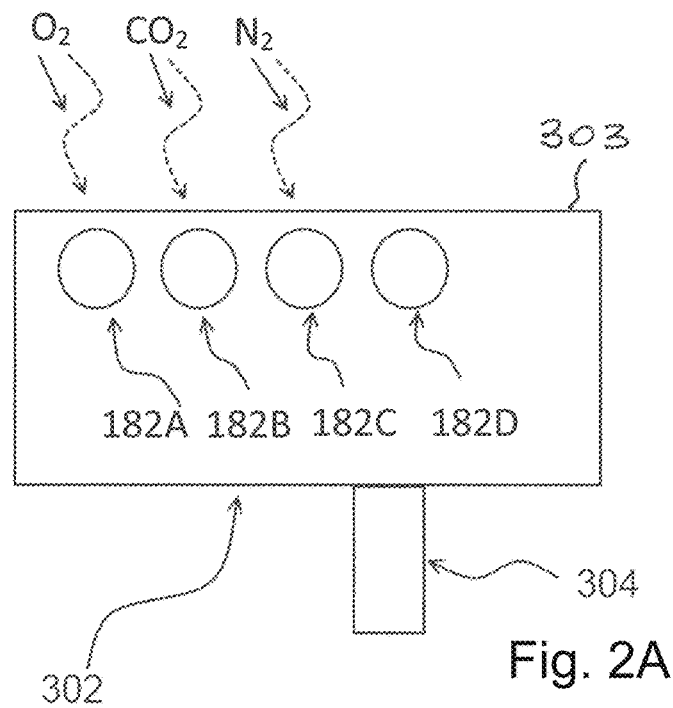
FIGS. 2A-2B illustrate exemplary devices for generating gas measurements using an array of solid state partial pressure measurement sensors or probes and a temperature sensor.
Figure 2B:
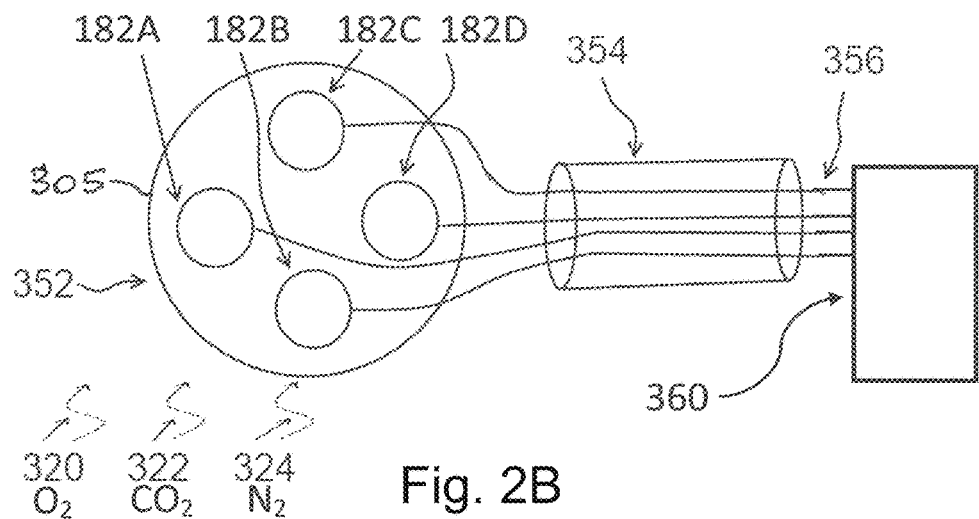

In an embodiment of FIGS. 2A-2B, therein are illustrated two diagrammatic views of exemplary devices 302, 352 comprising one or more solid state partial pressure sensors or probes 182A, 182B, 182C and thermistor 182D to measure one or more of oxygen 320, nitrogen 322, carbon dioxide 324 and temperature of the expirate 122 or the evacuated gas flow 172. The temperature measured is used as an input parameter for conversion of the solid-state partial pressure sensor signal into an absolute concentration measurement. The device 302 of FIG. 2A is illustrated as being mounted on a printed circuit board (PCB) 303 and is powered, during operation, through one or more input/output (I/O) cables 304 from a power source (not shown). The sensors 182A, 182B, 182C, and thermistor 182D can be disposed in any relationship to each other.

The device 352 of FIG. 2B is illustrated as comprising the partial pressure sensors 182A, 182B, 182C, and thermistor 182D being mounted on a support member 305. Wire 356 from each partial pressure sensors 182A, 182B, 182C, and thermistor 182D are formed into input/output (I/O) cable(s) 354 for a connection to a PCB (not shown) and/or a control device, for example such as a single board computer 692 in FIG. 6. The sensors 182A, 182B, 182C, and thermistor 182D can be disposed in any relationship to each other. This embodiment allows the sensors 182A, 182B, 182C, and thermistor 182D to be structurally detached from the PCB 360 to allow placement in a confined space(s) away from a wall surface thereof. For example, the sensors 182A, 182B, 182C, and thermistor 182D can be mounted inside the enclosure 193 away from the wall surface(s).

The device 302 or 352 is designed to operate while the RF emissions are activated or inactive.

Figure 3:
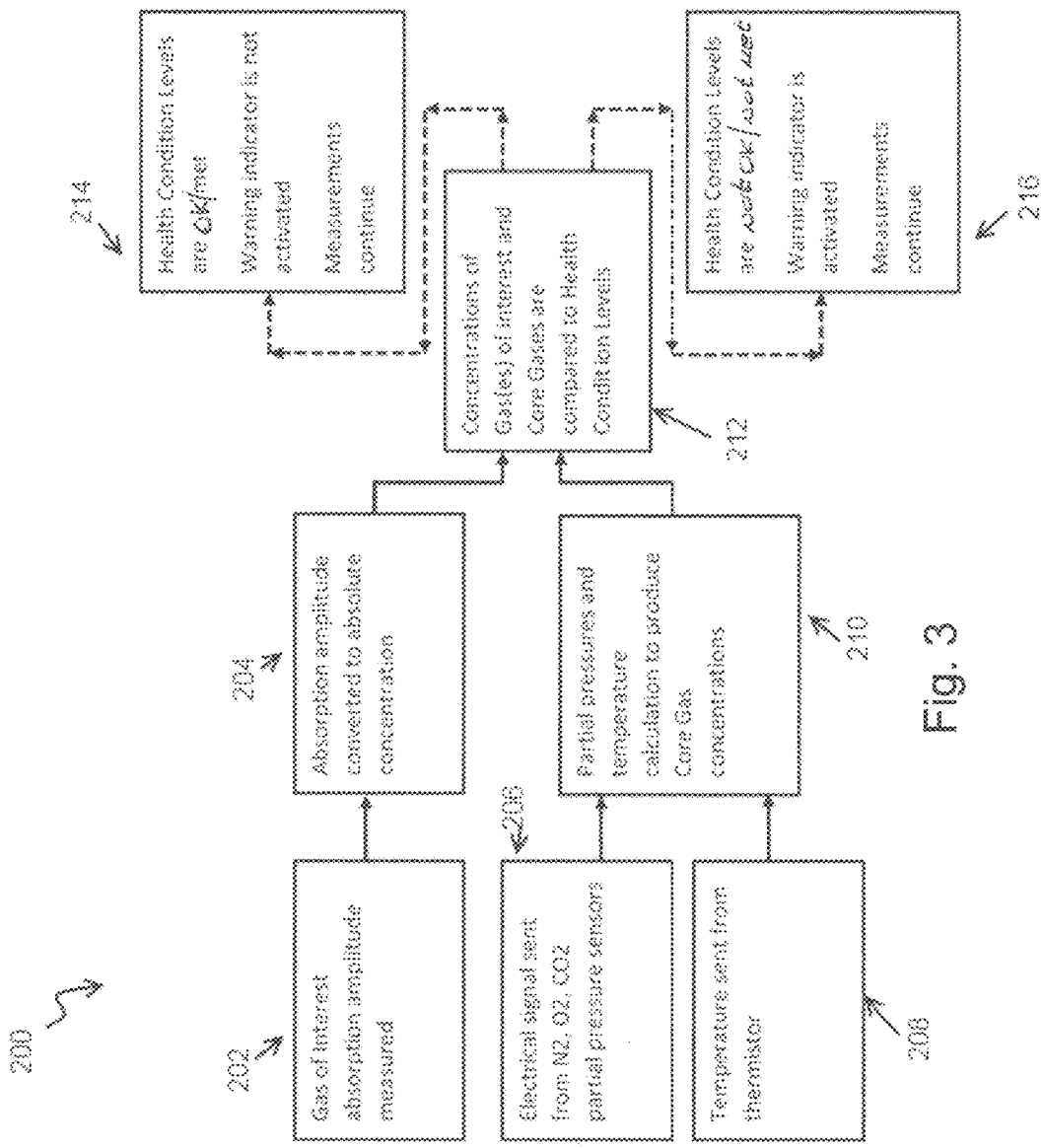
FIG. 3 illustrates a flowchart of an exemplary data processing and evaluation method for a chemical gas analysis and monitoring.

FIG. 3 illustrates a flowchart of an exemplary method to determine if measured gases correspond to gas levels associated with health or other conditions within a computer instructions or a computer program 200. The computer instructions or program employ one or more algorithms. The computer program can be executed within the general purpose processors 602 and/or single board computer 692 of FIG. 6. However, it is contemplated herewithin that a functionality of the general purpose processors 602 and single board computer 692 can be combined in a single control device or chip. In step 202, the program determines measured amplitude of absorption of gas(ses) and/or chemical mixtures of interest through analysis of the electromagnetic energy emission(s) received at the receive antenna 110. In step 204, the program converts the amplitude measured in step 202 to absolute concentration. In parallel, simultaneously, concurrently, or sequentially to step 202, the voltage signals from partial pressure sensors 182A, 182B and 182C are received in step 206 and the temperature voltage signal from the thermistor 316 are received in step 208. In step 210, the computer program converts the voltage signals received in steps 206 and 208 into absolute gas concentrations for oxygen, nitrogen, carbon dioxide and temperature, respectively. In step 212, the program evaluates the absolute concentrations from steps 204 and 210 to determine if the levels are comparable to Health Condition Levels (benchmark or threshold) of the gas(ses) of interest when the subject matter is related to medical use or other benchmark/threshold depending on the application. If the concentrations meet acceptable Health Condition Levels in a relationship to the device 102 of FIGS. 1A-1B or other conditions, in a relationship to the device 106 of FIG. 1C, a step 214 is performed by not activating a warning indicator and continuing measurement cycling. Step 216 is performed if the Health Condition Levels or other conditions are exceeded or not acceptable by the calculated concentrations by sending a signal to the warning indicator and continuing the measurement cycle. Examples of tangible warning indicators include, but not limited to any one of audio alarm, visual indicators, monitor warning message, system vibration, etc. Each step can be implemented as a module within the computer program.

Figure 4A:
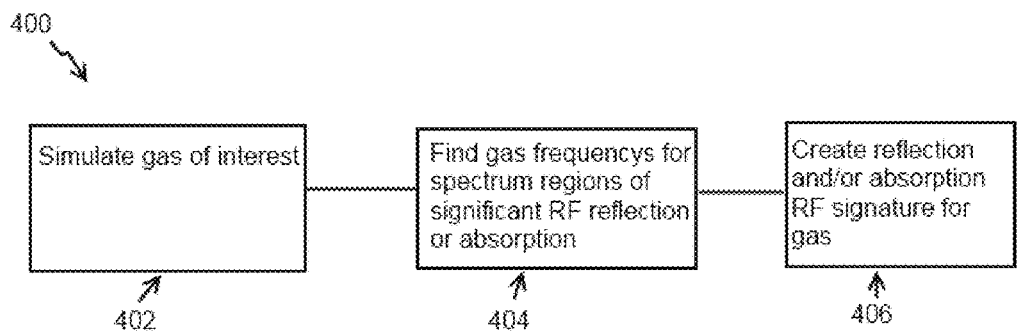
FIGS. 4A-4B illustrates two exemplary methods of generating a RF reflection and/or absorption signature for gas(es)
Figure 4B:
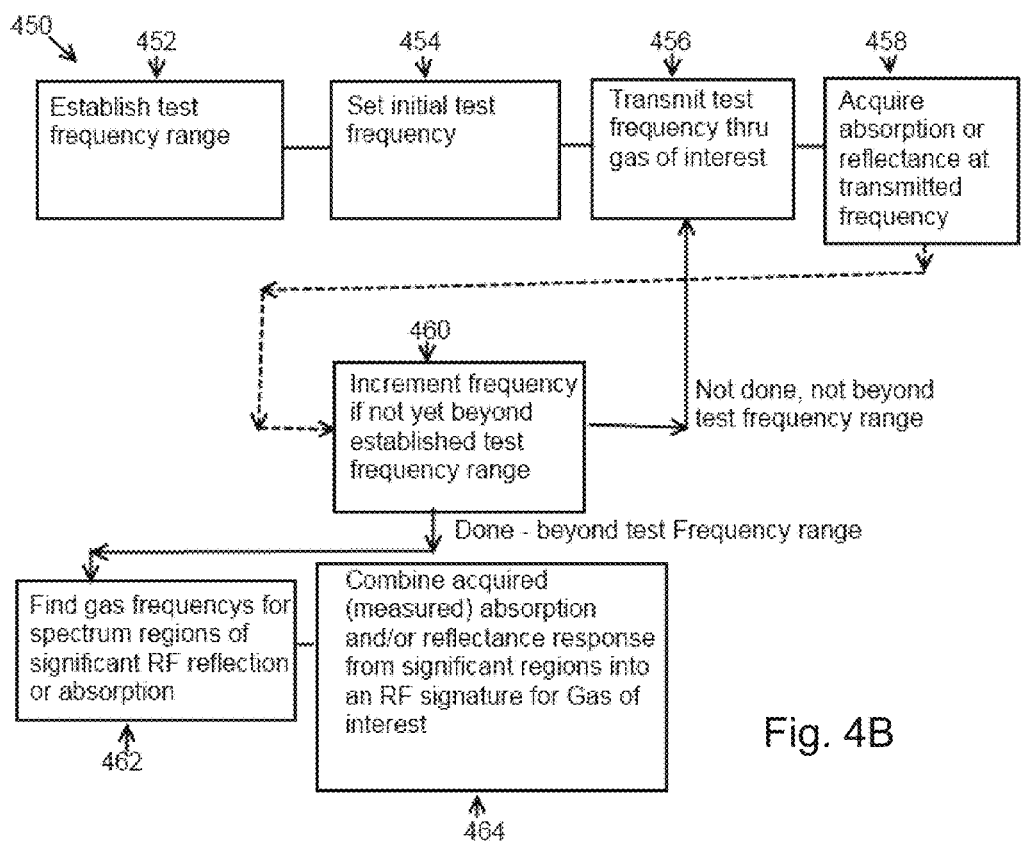

FIGS. 4A-4B illustrate flowcharts of two exemplary methods to generate an initial RF reflection and/or absorption reference signature for expirate 122 and or gas flow 172/174.

In a further reference to FIG. 4A, an exemplary method 400 describes the process for modeling chemical properties for the identification of RF absorption and/or reflection of spectral regions that can be exploited as signatures for chemical identification and/or quantification. Method 400 includes a step 402 of simulating the chemical of interest using modeling algorithms and/or software. In step 404, the simulation of the chemical(s) of interest is used to identify electromagnetic frequencies that are absorbed or reflected by the chemical(s) of interest within a software entity instead of a hardware entity. In step 406, a combination of reflection and/or absorption energies are combined to identify characteristics in RF and microwave frequency space to use as a verification signature that can be used with or without a secondary verification signature for the identification and/or quantification of the chemical(s) of interest.

A variety of software simulation means are available to generate the gas molecule spectrum enabling identification of its spectral frequency regions of significance or interest which exhibit absorption or reflection at frequency regions significantly differing from the absorption or reflection from other regions, useless regions typically exhibit a variation in absorption or reflection of less than 3 dB at 100% concentration. Useful software simulation to apply to generate the spectrum may include Density Function Theory (DFT) models, TD/DFT models, Gaussian98, Amsterdam Density Functional (ADF), MNOVA, Spartan, etc. The spectra to be used in the signature and to be emitted by the transmit antenna may also be found on the internet in spectral libraries, and/or through websites such as www.MassBank.jp.

In a further reference to FIG. 4B, an exemplary method 450 describes the process for experimentally measuring chemical properties regarding electromagnetic wave frequencies absorbed and/or reflected by the chemical(s) within gases of interest. Method 450 comprises a step 452 of establishing a frequency region to experimentally evaluate the chemical(s), setting the hardware component to an initial test frequency in step 454 and transmitting electromagnetic waves (emissions) determined in step 452 through the chemical(s) of interest in step 456. Transmitted and/or reflected electromagnetic waves are measured after interacting with the chemical(s) of interest to calculate absorption and/or reflectance of the frequency region under test in step 458. The transmitted frequency region under test is incremented and measured for the test range established in step 452. Frequencies and/or regions of frequencies are identified that have absorption and/or reflection properties that can be used for developing a verification signature that can be used with or without a secondary verification signature for the identification and/or quantification of the chemical(s) of interest in step 462. Step 464 combines the measured absorption and/or reflection response frequencies into one or more verification signature(s).

Figure 5:
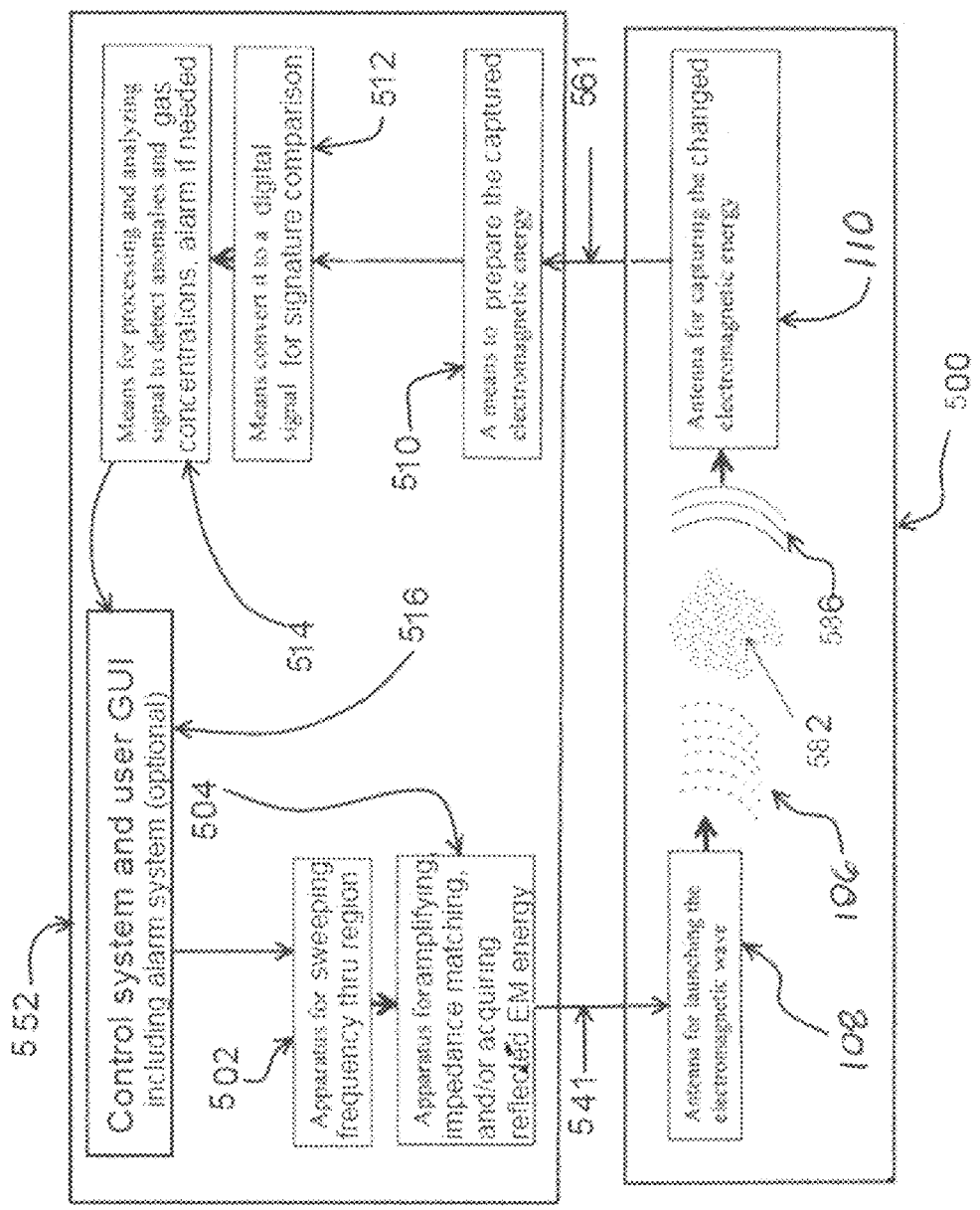
FIG. 5 illustrates a block diagram of an exemplary embodiment of a hardware and software architecture configured to control and enable chemical gas concentration analysis and monitoring.

FIG. 5 illustrates both a diagram of an exemplary apparatus and a flowchart of an exemplary method of a control system and user GUI that controls the hardware/software component 552 and/or hardware component 500. The hardware/software component 552 comprises an apparatus 502 that is configured to generate the frequency of the transmitted electromagnetic wave 106. The apparatus 502 can be anyone of a Direct Digital Synthesizer (DDS), Voltage Controlled Oscillator (VCO), Signal generator with frequency sweep capability, Function generator with frequency sweep capability, or similar. The hardware/software component 552 also comprises apparatus 504 configured to amplify, match impedance of, and/or acquire electromagnetic energy. The apparatus 504 can be an RF amplifier and/or a means for impedance matching such as a Balun if needed, and/or a Directional coupler to acquire the reflected RF energy, and/or filters such as bandpass, high pass, low pass to reduce unwanted frequencies from the apparatus 502 or amplifier caused by harmonic distortion for example. The hardware/software component 552 also comprises a means or a component 510 for preparing captured electromagnetic energy 586. The means or the component 510 can comprise one or more of a bandpass, high pass, low pass to reduce unwanted frequencies from the environment, a Low Noise Amplifier (LNA), frequency pre-selector, an impedance matcher such as an RF transformer or Balun, etc. The hardware/software component 552 also comprises a means or a component 512 for converting the captured electromagnetic energy field/wave signal into a digital signature for comparison purposes. The means or the component 512 can be an A/D converter. The hardware/software component 552 also comprises a means or a component 514 for processing and analyzing the captured signal to detect anomalies and/or chemical gas concentrations and/or alarm signal generation. The means or the component 514 can comprise one or more algorithm, such as a Fourier Transform, a fast Fourier transform (FFT), a frequency peak detection, a signature comparison, a Non-coherent integration, a pattern recognition and the like evaluation algorithms.

The hardware control component 500 includes the above described antenna 108 for transmitting electromagnetic energy emission or field/wave/spectrum 106, the reflected/influenced electromagnetic energy field/wave 586 after the electromagnetic wave emission 106 is passed through the chemical(s) of interest 582 and the receive antenna 110 for receiving/capturing the electromagnetic energy field/wave 586. The electromagnetic wave 106 may or may not be altered through interactions with the chemical(s) of interest 582 as the resulting electromagnetic wave 586.

The hardware/software component 552 and/or hardware component 500 can be configured as comprising one or more circuits.

FIG. 5. Also illustrates an embodiment of a closed-loop control system and/or method between the hardware/software component 552 and the hardware component 500 by comprising a signal 541 to the hardware component 500 to generate transmission of the electromagnetic wave 106. Additionally, the exemplary control system also includes the captured electromagnetic wave signal 561 from the antenna 110 to the means of signal acquisition 510.

FIG. 6 illustrates a block diagram of an exemplary apparatus 650 configured to detect, characterize and/or quantify concentration(s) of chemical(s) of interest. FIG. 6 also illustrates an exemplary method for detecting, characterizing and/or quantifying concentration(s) of chemical(s) of interest.

The apparatus 650 comprises an apparatus 620A configured to perform conversions to and/or from time domain data to frequency domain, as well as to interact with components such as the GUI and/or alarm 622, tuner/filter 687, electromagnetic illumination frequency oscillator 636, and analog to digital converter(s) 638. The apparatus 620A comprises a single or a multi-board computer or controller 692 that communicates with the general-purpose processors 602 that receive signals from the analog to digital converters 638, optional DSP ICs 604, and adjust optional filter settings

687. An optional digital signal processor ICs 604 can send and/or receive signals from the programmable logic device 606 and the general-purpose processors 602 to speed up the math performed in signature comparison algorithms for example. Single Board Computer 692 is also configured to receive optional voltage reference signals from sensors 182A, 182B, 182C and/or thermistor 182D.

The apparatus 650 can be configured as comprising one or more circuits.

An exemplary RF chain can include the illumination frequency oscillator 636, the RF power amplifier 634, the optional directional coupler 632, the transmit antenna 108, the transmitted electromagnetic wave 106, the chemical(s) or chemical mixture 582 of interest, the transmitted electromagnetic wave 586 after interacting with the chemical(s) of interest 656, the receive antenna 110, the low noise amplifier(s) (LNA) 626, the RF tuner(s) 644, the analog to digital converter(s) 638, and the optional filter(s) 687. Using LNA 626, with a noise figure under 2 dB and an FFT size of 16K or greater, a sensitivity level better than −150 dBm in the receiver 650 can be achieved. This sensitivity enables detection of low concentrations of gasses and/or the use of lower illumination energy to achieve an illumination exposure under the level considered hazardous or unacceptable by Government standards. Another method of improving sensitivity is using Non-coherent integration (NCI), wherein a smaller FFT, longer NCI integration time and samples, and/or use of higher illumination power. With improved sensitivity, the FFT size can the reduced and/or the dBm sensitivity level can be reduced. The single or a multi board computer or controller 692 can be configured to control the illumination frequency oscillator's frequency 636 that sends the RF signal to the RF power amplifier 634. The amplified signal is optionally sent to the directional coupler 632 or the transmit antenna 108. An RF directional coupler 632 may be used to acquire the reflected spectral energy of the gas under test while allowing the illumination frequency energy to proceed thru the gas. This allows the low level reflected RF energy to be separated from the high-level illumination energy, enabling a more sensitive measurements of the reflected energy. The electromagnetic wave 106 transmitted from the antenna 108 reacts with the chemical(s)/gas(ses) 582 of interest and is either reflected to the transmit antenna 108 and to the optional directional coupler 632 or an electromagnetic wave 586 after interaction with the chemical(s) or mixture of interest 582 is received by a receive antenna 110. The signal from the receive antenna 110 and/or the optional directional coupler 632 is sent to the low noise amplifier(s) 626 then passed to the RF tuner(s) 644. The RF tuner(s) 644 receive filter settings from filter 687 and pass the resulting signal to the analog to digital converter(s) 638. The digital signal is received by the apparatus 620A to convert time domain data into frequency domain data through the programmable logic device 606. After conversion, the signal is passed to the general-purpose processor 602 and the single or a multi board computer or controller 692. The controller 692 performs any verification using one or more verification signature(s) and can displays the result(s) on the optional GUI display and/or alarm 622.

It is contemplated herewithin that any combination of the components 602, 604, 606, 626, 638, 644, 687, and 692 can be integrated into a single control member integrated into a computer and/or implemented as system on a chip.

Figure 7:
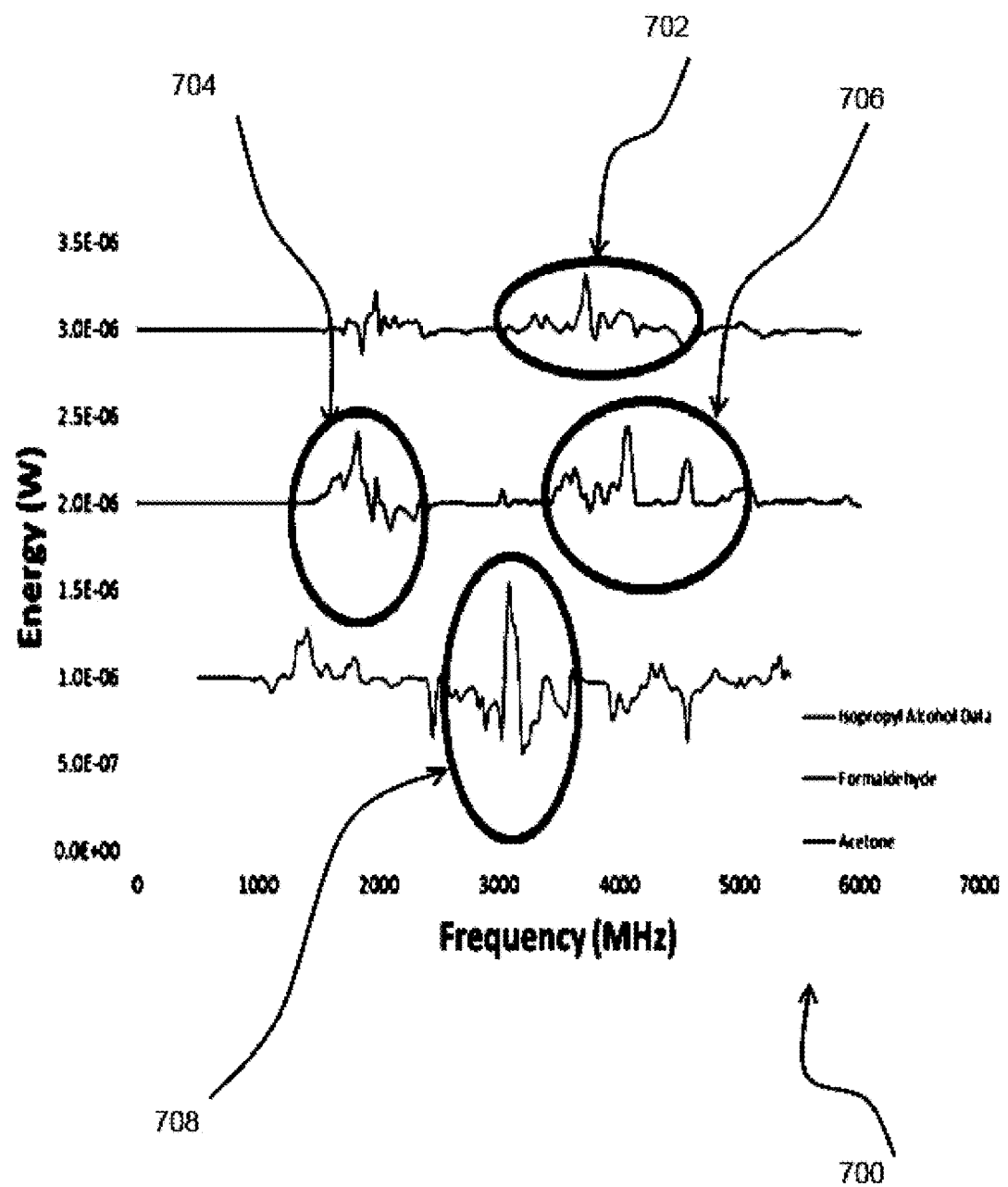
FIG. 7 illustrates several microwave and radio frequency absorption spectrum features of chemicals in gas form that are used for identification and quantification measurements.

FIG. 7 illustrates several microwave and radio frequency absorption features of chemicals in gas form that are used for identification and quantification measurements. Specifically, the absorbed energy 700 of isopropyl alcohol, formaldehyde, and acetone. Features of absorbed energy at specific frequencies, 702 for isopropyl alcohol, 704 and 706 for formaldehyde, and 708 for acetone, can be used to create one or more verification signature tools to identify and/or measure concentration(s) of these chemical(s) of interest.

An exemplary verification signature tool for acetone could include, but not limited to, the frequency position, shape of the absorption peak, amplitude of the absorption peak, etc. In general, the verification signature (tool) for any chemical, chemical mixture, gas and/or expirate 122 can comprise one or more spectral features, such as 704 and/or 706 and/or 708, as a basis for identifying and/or measurement of concentration(s) of these chemical(s) of interest.

Figure 8:
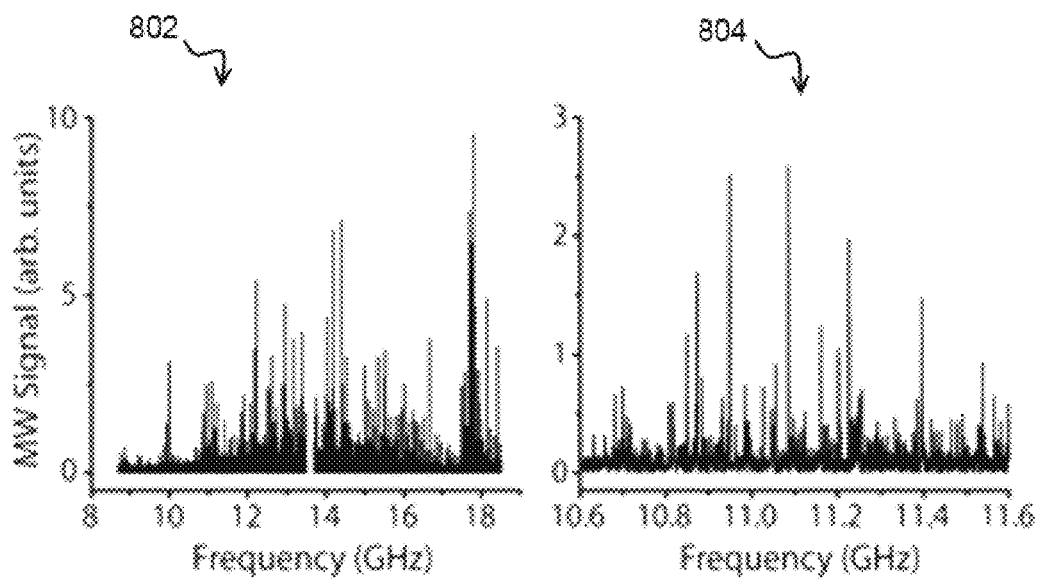
FIG. 8 illustrates exemplary samples of chemical RF absorption spectra and a non-inclusive list of chemicals characterized by RF spectroscopy.

FIG. 8 illustrates RF absorption features of propanol from a span of 8 to 18 GHz 802, in addition to a smaller span of 10.6 GHz to 11.6 GHz 804. A non-inclusive list of chemicals that have been characterized with RF spectroscopy with identifiable spectral characteristics that can be used to create one or more verification signature tool(s) 806.

An exemplary approach/method for determining chemical concentration through RF absorption and/or reflection measurements is explained below.

The ability of a specific material or chemical to absorb energy at a particular frequency is given by its loss tangent, tan δ, at that frequency. The loss tangent is tied directly to the permittivity of a material in the following manner. Permittivity can have a real and imaginary component and is expressed as:

$$\epsilon = \epsilon' - j\epsilon''$$

Where j is the square root of −1. The loss tangent is then defined by as:

$$\tan\delta = \frac{\omega \epsilon'' + \sigma}{\omega \epsilon'}$$

where ω is the angular frequency of the wave, and σ is the free charge conduction the gas(ses) under test. From this, it is clear that the loss tangent response profile is highly frequency dependent, with large values indicating strong absorption at that particular frequency. Additionally, microwave absorption follows the Beer-Lambert relationship:

Where γ is the frequency dependent absorption coefficient, I0 is the initial signal intensity, and x is the path length. The absorption coefficient is given by the Van Vleck-Weisskopf equation:

$$Y = \frac{8\pi^2 Nf}{3CkT}(u_{ij})^2 v^2 \frac{\Delta v}{(v-v_0)^2 + (\Delta v)^2}$$

Where N is the number of molecules per unit distance traveled in medium, $u_{ij}$ is the dipole matrix element connecting the upper and lower energy states and v is the energy state transition frequency. The absorption coefficient is therefore linearly dependent on the number of molecules present. Since the absorption coefficient is in the exponent of the Beer-Lambert equation, the relationship between chemical concentration, makeup, or degree of degradation and absorbed microwave energy may appear linear when absorption is measured on a logarithmic scale (e.g. frequency in GHz vs. absorption loss in dB).

FIG. 9A illustrates an exemplary embodiment of an apparatus 1010 comprising a hardware and software architecture/apparatus and apparatus to process the received RF radiation for gas concentration determination/estimation. Specifically, the apparatus 1010 comprises the LNA 626, RF tuner 644 and Analog to Digital converter 638. The apparatus 1010 can be referred to as a receiver of the electromagnetic energy emission captured by the receive antenna 110. The apparatus 1010 also comprises one or more processors and a non-transitory computer readable medium comprising executable instructions that, when executed by the one or more processors, cause the one or more processors to perform various method steps.

FIG. 9A also illustrates an exemplary method/process for processing captured electromagnetic energy emission signal in order to determine any concertation of the chemical and/or gas mixture.

The method comprises a step of converting the captured and received electromagnetic energy emission signal from an analog to digital signal that processes the captured digital signal by converting the digital time domain signal to a frequency domain signal in module 1026, comprising digital filter 1034, signal processing 1032 and wavelet de-noising 1030. The signal is then filtered with additional signal processing module 1027, comprising digital filter 1052 and additional signal processing 1054. The processed signal is evaluated and scored according to module 1028 comprising one or more algorithms 1040, a frequency domain algorithm waiting 1050 and a determining/calculating final evaluation score 1028.

FIG. 9B illustrates an exemplary embodiment of a method 1068 comprising one or more algorithms (executable instructions) that can be embedded into the detection apparatus, for example such as the apparatus 650. A spectral signature is processed from collected RF signal in step/module 1072 and compared against the template 1070 using algorithm(s) 1074 to determine the presence and/or quantity of the gas(ses) under test in step or module 1076. The result of detection may result in an alarm or other alert 1078 sent to the user as needed or displayed on the GUI 622.

In an embodiment, an apparatus and/or a method detects levels of acetone in human expirate. Although acetone is present in exhaled gases, certain levels of Acetone in the human expirate may indicate a heart failure condition. Thus, in an embodiment, an apparatus and/or a method detect a heart failure condition is created.

In an embodiment, an apparatus and/or a method can be used for analysis of medical conditions in humans or animals alike.

In an embodiment, an apparatus and/or a method can be used for analysis of ozone levels in air for safety reasons.

In an embodiment, an apparatus and/or a method can be used for analysis of pollutions levels.

In an embodiment, an apparatus and/or a method can be used for analysis of methane levels.

In an embodiment, an apparatus and/or a method can be used for analysis of hydrazine levels.

In an embodiment, an apparatus and/or a method can be used for analysis organic and non-organic gases.

In an embodiment, the apparatus for measuring and/or analyzing gases can be configured as a wearable apparatus. In an example, a patient equipped with mask 102 can have the control and measurement apparatus configured to be worn on a belt or disposed in a pocket of a garment. In an example, a diver equipped with the mask 102 can have the control and measurement apparatus disposed within the mask or within the diving apparatus.

In an embodiment, the apparatus for measuring and/or analyzing gases can be configured as a portable apparatus. In an example, a patient equipped with mask 102 can have the apparatus configured to be moved for example on a support during patient's movement.

In an embodiment, the apparatus for measuring and/or analyzing gases can be configured as a stationary apparatus.

The stationary apparatus can be coupled by wires or wirelessly with the devices 102, 192.

In an embodiment, a single or a multi-board computer or controller 692 can be configured and/or integrated within a mobile communication device, for example such as a mobile phone, an iPad, a tablet and the like.

In an embodiment, a single or a multi-board computer or controller 692 can be configured and/or integrated within a portable hand held device.

In an embodiment, any of the above described embodiments can be implemented or configured as a sensor.

It is to be understood that a substantially identically configured system containing a substantially identical RF and executing in parallel may be used to generate exemplary RF emissions and form or determine an exemplary basis for emission characteristics of all substantially similarly configured devices. Thus, the specific RF generating device response need not be initially analyzed in the RF emission domain to later verify its emission comparison. An exemplary device's resulting RF emission may be previously, currently or later analyzed to determine, verify or predict the expected RF emission response of a different yet substantially identically configured unit. The RF emission may be recorded and later verified against an exemplary emission, and need not be immediately evaluated. The RF emissions may thus be recorded in the time domain for later FFT processing and analysis or comparison/verification in the time and/or frequency domain.

In an embodiment two and only two antennas can be operable.

In an embodiment, three and only three antennas can be operable.

Horn antennas, when used, are pointed toward each other. So too are spiral, dipole/monopole antennas The optional components to the embodiments of the invention, the solid-state oxygen, nitrogen, and carbon dioxide sensors and the thermistor are used in some embodiments of the invention that require oxygen, nitrogen, and carbon dioxide concentrations for detection, analysis, or quantification purposes. An exemplary embodiment that includes these optional components, in addition to the RF antenna signal measurements, is for a device that measures exhaled breath for the determination of pulmonary oxygen toxicity, in which oxygen, and/or nitrogen, and/or carbon dioxide levels of exhaled breath may change. In this embodiment, the thermistor is used with the solid-state sensor to convert the signal to a concentration measurement. Each solid-state sensor may be used with or without the other sensor(s) in an embodiment.

The embodiments are not predisposed to an orientation of use by the apparatus.

In an embodiment, the RF antenna(s) are exposed to the open environment, with or without the optional solid-state sensors and thermistor.

In an embodiment, the RF antennas can be in a confined space, with or without the optional solid-state sensors and thermistor. The confined space would ideally have EMI shielding, but is optional.

In an embodiment, a mask with two antennas with the solid-state sensors and thermistor are used to detect PO2T of the diver, with a vibrational and acoustic alarm.

In an embodiment, an enclosure with two antennas with the solid-state sensors and thermistor are used to monitor premature infants for PO2T with a visual, and acoustic alarm.

In an embodiment, two antennas are used in a small, ventilated enclosure to detect hydrazine in a space shuttle cabin, with a visual alarm.

In an embodiment, two antennas are placed around a breathing tube on a hand-held device to monitor expirate for human health conditions, including, but not limited to pulmonary oxygen toxicity, heart failure, diabetes, ulcerated colitis, and/or cancer.

In an embodiment, any of the above described apparatus can be configured with a sensitivity below −149 dBm, allowing for lower microwave transmit power to be used to achieve the substantially same spectral measurement and hence substantially same spectrum processing and analysis result as with less sensitive implementations. When the apparatus is configured with such reduced sensitivity, the reduced dBm level of the transmitter creates a correspondingly reduced received spectrum dBm level. This reduced dBm received spectrum level enables a lower microwave exposure to the patient to be within or under Government microwave safe exposure limits for humans. Thus a mask or apparatus incorporating the invention's gas sensing technology in close proximity to patients or hospital personnel is safe to use, lighter in weight as lower power cabling, less RF shielding, no RF shielding, and lower power draw is required. The lower power draw also allows for a smaller battery and/or a lighter weight device in a portable embodiment.

In an embodiment, the microwave energy is absorbed, reflected, and re-emitted at lower frequencies, creating the measured spectral response indicative of a concentration and presence of a specific gas compound's molecule.

In an embodiment, a means such as non-coherent integration can be used to improve the spectrum analysis result by reducing the noise level content relative to emission signal content in the received spectrum. A greater receive sensitivity, reduced illumination power levels, and improved detection accuracy results may thus be effectively achieved by using non-coherent integration, but this may be a trade-off requiring more time for acquisitions and processing, and/or may require additional RF receive channels. Longer Coherent-integration means may also be similarly used to improve sensitivity, reduce illumination power levels, and/or improve detection accuracy results.

In an embodiment, each solid-state sensor may be used with or without the other sensor(s). In this embodiment, RF spectroscopy measurements of gasses that are polar and non-polar in nature is combined. Non-polar molecules, such as oxygen, nitrogen, and carbon dioxide, can be detected with RF spectroscopy to some degree, however, the measurable concentrations of the targeted polar molecules are expected to be several orders of magnitude smaller than the non-polar molecules in some embodiments.

Another advantage of solely using only the RF absorption gas measurement means as opposed to using both the solid-state gas sensor measurement means and also the RF absorption gas measurement means is the reduction in total hardware used. Because the wide variety and range of molecules measurable solely by the RF absorption gas measurement means include those measurable by the solid-state gas sensors, using only the RF absorption gas measurement means may be used without additional gas measurement sensors. However, the optional solid-state sensors may significantly improve measurement speed by simultaneously, quickly and easily measuring the higher composition gases of the bulk gases. Stated another way, these optional solid-state sensors require more space and weight but less computational costs and/or measurement acquisition time to determine gas concentrations than a device constructed which uses the RF absorption gas measurement device alone. However, by utilizing these optional sensors, the apparatus may become more efficient The non-polar molecules, such as oxygen, nitrogen, and carbon dioxide, can be detected without the use of the optional solid-state sensors in some embodiments.

The embodiments are not predisposed to an orientation of use by the apparatus.

In an embodiment, the RF antennas are exposed to the open environment, with or without the optional solid-state sensors and thermistor.

In an embodiment, the RF receive and transmit antennas are not shielded within a Faraday cage.

In an embodiment, the RF antennas are in a confined space, with or without the optional solid-state sensors and thermistor. The confined space would ideally have EMI shielding or comprised of a Faraday cage, but is optional.

In an embodiment, an apparatus for determining a concentration of gasses in a gas mixture comprises a transmit antenna coupled to the at least one microwave generator, the transmit antenna configured to transmit an electromagnetic energy emission spectrum through the gas mixture in a response to a microwave radiation coupled thereto; at least one microwave generator tuned to responsive frequencies of the gas, the at least one microwave generator configured to couple the microwave radiation to the transmit antenna; a receive antenna configured to capture an electromagnetic energy difference between a transmitted electromagnetic energy emission spectrum and an electromagnetic energy emission spectrum being absorbed or reflected by gaseous molecules in the gas mixture; a receiver coupled to the receive and/or transmit antenna, the receiver configured to convert the electromagnetic energy difference, into a digital signal; and a control member configured to process the digital signal in accordance with one or more algorithms, the control member configured to analyze the electromagnetic energy difference and determine concentration(s) of gasses in the gas mixture based on an analysis of the difference.

A feature of this embodiment is that the control member is configured to identify a presence or an absence of a heart failure condition in a subject in a response to measuring concentrations of Acetone, and/or Pentane, and/or Hexane, and/or Propane, and/or NO+, and/or Oxygen, and/or Nitrogen, and/or Carbon Dioxide and computationally combining the concentrations measured into an overall score indicative of a degree of or a probability of the heart failure condition in the subject.

A feature of this embodiment is that the control member is configured to identify a presence or an absence of a Pneumonia condition in a subject in a response to measuring concentrations of gasses Isoprene, and/or Hydrogen Cyanide, and/or Oxygen, and/or Nitrogen, and/or Carbon Dioxide and computationally combining the concentrations measured into an overall score indicative of a degree of or probability of the Pneumonia condition in the subject.

A feature of this embodiment is that the control member is configured to identify a presence or an absence of a Pulmonary Oxygen Toxicity condition in a subject in a response to measuring the concentrations of gasses 3-meythyltridecane, and/or 3-methyltridecane, and/or 5-methylnonane, and/or Oxygen, and/or Nitrogen, and/or Carbon Dioxide and computationally combining the concentrations measured into an overall score indicative of a degree of or probability of the Pulmonary Oxygen Toxicity condition in the subject.

A feature of this embodiment is that the control member is configured to determine a relationship between a concentration of gas compounds.

A feature of this embodiment is that the control member is configured to determine an intensity of compound absorption or reflection spectrum in a form of a calibration curve.

A feature of this embodiment is that the control member is configured to the subject the electromagnetic energy emission spectrum to a Fourier analysis.

A feature of this embodiment is that the microwave generator includes at least one of a microwave synthesizer, a directional coupler, a circulator, and a microwave amplifier connected to an output of the microwave synthesizer.

A feature of this embodiment is that the control member comprises a non-coherent and a coherent integration signal processing to reduce a sensitivity of the apparatus.

A feature of this embodiment is that the sensitivity of the apparatus is below −149 dBm.

A feature of this embodiment is that emitted microwave radiation level is maintained below a Specific Absorption Rate (SAR) mandated in accordance with a predefined standard for a person wearing the apparatus in an intended manner where the apparatus is operable as a measurement device. For example, in USA, FCC limit for public exposure from cellular telephones is an SAR level of 1.6 watts per kilogram (1.6 W/kg). A feature of this embodiment is that the transmit antenna being further configured to receive an electromagnetic energy emission spectrum reflected by the gas mixture, the receiver being further configured to receive electromagnetic energy emission spectrum reflected by the gas mixture and received by the transmit antenna and convert the reflected electromagnetic energy emission spectrum into the digital signal.

In an embodiment, a method is provided for determining a presence or an absence of a medical condition in a patient, the method comprises the steps of passing an electromagnetic field generated by a pair of spaced apart antennas through an expirate from the patient; measuring at least one of an absorption amplitude, an emission amplitude and a reflection amplitude of the expirate from the patient from the electromagnetic field; converting the at least one of the absorption amplitude, the emission amplitude and the reflection amplitude to an absolute concentration; comparing absolute expirate concentration against a stored value; and determining the presence or the absence of the medical condition based on a results of a comparison of the absolute expirate concentration against the stored value.

A feature of this embodiment is that the step of passing the electromagnetic field comprises a step of generating microwave radiation at one or more frequencies the expirate is most responsive.

A feature of this embodiment is that the step of measuring comprising a step of receiving, with a receiving antenna, a microwave radiation transmitted through the expirate.

A feature of this embodiment is that the step of measuring comprising a step of measuring absorption and/or reflection of the microwave radiation.

In an embodiment, a mask comprises a member; a pair of antennas mounted on a surface of the member or within a thickness thereof in a spaced apart relationship with each other; one or more sensors mounted on or within the member; and a ventilation member coupled to the member.

In an embodiment, an apparatus comprises a mask comprising a member, a pair of antennas mounted on a surface of the member or within a thickness thereof in a spaced apart relationship with each other, one or more sensors mounted on or within the member, and a ventilation member coupled to the body. The apparatus further comprises a control member configured to measure absorption, emission and/or reflection of electromagnetic energy spectrum influenced by gaseous molecules in an expirate, the control member configured to determine concentration of gasses in the expirate based on a measurement of one or more of the absorption, the emission and the reflection of the electromagnetic energy spectrum.

In an embodiment, a method for analyzing gaseous compounds and/or for determining a concentration of gas(es) in a gas mixture comprises the steps of generating a microwave radiation at one or more frequencies the gas mixture is most responsive to; transmitting, with a transmitting antenna, the generated microwave radiation through the gas mixture; receiving, with a receiving antenna, a resulting microwave radiation transmitted through the gas mixture; and measuring absorption and/or reflection of the microwave radiation.

A feature of this embodiment is that measuring of the absorption and/or the reflection of the microwave radiation comprises using a fast Fourier Transform (FFT) spectrum versus an energy response generated, the response subsequently used to calculate gas concentration.

In an embodiment, any of the above described methods can be implemented in the form of software or a computer program stored on a tangible computer-readable non-transitory information storage medium and can be implemented in general-use digital computers that execute the programs using a computer readable storage and/or recording medium. In other words, in the context of this document, a computer readable storage and/or recording medium may be any tangible medium that can contain, or store a program and/or data for use by or in connection with an instruction execution system, apparatus, or device.

Tangible computer readable medium means any physical object or computer element that can store and/or execute computer instructions. Examples of tangible computer readable medium include, but not limited to, a compact disc (CD), digital versatile disc (DVD), blu-ray disc (BD), USB floppy drive, floppy disk, random access memory (RAM), read-only memory (ROM), erasable programmable read-only memory (EPROM), optical fiber, etc. In other words, tangible computer readable medium may be an internal part of the computer, a removable external element coupled to the computer, or unit that is remotely accessible via a wired or wireless network. It should be noted that the tangible computer readable medium may even be paper or other suitable medium in which the instructions can be electronically captured, such as optical scanning. Where optical scanning occurs, the instructions may be compiled, interpreted, or otherwise processed in a suitable manner, if necessary, and then stored in computer memory. Alternatively, tangible computer readable medium may be a plugin or part of a software code that can be included in, or downloaded and installed into a computer application. As a plugin, it may be embeddable in any kind of computer document, such as a webpage, word document, pdf file, mp3 file, etc.

Any combination of one or more computer readable storage medium(s) may be utilized. A computer readable storage medium may be embodied as, for example, an electronic, magnetic, optical, electromagnetic, infrared, or semiconductor system, apparatus, or device, or other like storage devices known to those of ordinary skill in the art, or any suitable combination of computer readable storage mediums described herein. The non-transitory computer-readable recording medium may include program instructions, data files, and data structures, alone or in a combination thereof.

In an embodiment, any of the above described methods can be implemented by a single or multiple algorithms.

Persons of ordinary skill in the art may appreciate that, in combination with the examples described in the embodiments herein, units and algorithm steps can be implemented by electronic hardware, computer software, or a combination thereof. In order to clearly describe the interchangeability between the hardware and the software, compositions and steps of every embodiment have been generally described according to functions in the foregoing description. Whether these functions are performed using hardware or software depends on particular applications and design constraints of the technical solutions. A person skilled in the art may use different methods to implement the described functions for each specific application. However, such implementation should not be considered as beyond the scope of the present invention. As an example, the same circuit capabilities may be made in an ASIC, FPGA, or custom logic device.

Computer program code for carrying out operations for aspects of various embodiments may be written in any combination of one or more programming languages, including an object oriented programming language, such as Java, Smalltalk, C++, or the like, and conventional procedural programming languages, such as the "C" programming language or similar programming languages. In accordance with various implementations, the program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

It will be understood that various blocks of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Many of the elements described in the disclosed embodiments may be implemented as modules. A module is defined here as an isolatable element that performs a defined function and has a defined interface to other elements. The modules described in this disclosure may be implemented in hardware, software in combination with hardware, firmware, wetware (i.e hardware with a biological element) or a combination thereof, all of which are behaviorally equivalent. For example, modules may be implemented as a software routine written in a computer language configured to be executed by a hardware machine (such as C, C++, Fortran, Java, Basic, Matlab or the like) or a modeling/simulation program such as Simulink, Stateflow, GNU Octave, or Lab VIEWMathScript. Additionally, it may be possible to implement modules using physical hardware that incorporates discrete or programmable analog, digital and/or quantum hardware. Examples of programmable hardware comprise: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies are often used in combination to achieve the result of a functional module.

The chosen exemplary embodiments of the claimed subject matter have been described and illustrated, to plan and/or cross section illustrations that are schematic illustrations of idealized embodiments, for practical purposes so as to enable any person skilled in the art to which it pertains to make and use the same. It will be understood that variations, modifications, equivalents and substitutions for components of the specifically described exemplary embodiments of the disclosed subject matter may be made by those skilled in the art without departing from the spirit and scope of the subject matter as set forth in the appended claims.

When used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Although the subject matter has been described in a combination with RF emissions, the disclosed embodiments will apply to devices emitting microwave emissions, millimeter wave emissions and terahertz wave emissions.

It should be appreciated that reference throughout this specification to "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment or the same variation. Furthermore, the particular features, structures or characteristics may be combined as suitable in one or more embodiments of the invention.

Similarly, it should be appreciated that in the foregoing description of embodiments of the invention, various features are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claimed subject matter requires more features than are expressly recited in each claim. Rather, as the following claims reflect, inventive aspects lie in less than all features of a single foregoing disclosed embodiment. Thus, the independent claims following the detailed description are hereby expressly incorporated into this detailed description.

Any element in a claim that does not explicitly state "means for" performing a specified function, or "step for" performing a specified function, is not to be interpreted as a "means" or "step" clause as specified in 35 U.S.C. § 112, 6. In particular, any use of "step of" in the claims is not intended to invoke the provision of 35 U.S.C. § 112, 6.

Anywhere the term "comprising" is used, embodiments and components "consisting essentially of" and "consisting of" are expressly disclosed and described herein." Furthermore, the Abstract is not intended to be limiting as to the scope of the claimed invention and is for the purpose of quickly determining the nature of the claimed invention.

What is claimed is:

1. An apparatus for determining a concentration of gasses in a gas mixture, said apparatus comprising:
   a hollow enclosure;
   an intake member attached to said hollow enclosure, said intake member configured to introduce the gas mixture into said hollow enclosure;
   an evacuation member attached to said hollow enclosure, said evacuation member configured to evacuate the gas mixture from said hollow enclosure;
   at least one microwave generator tuned to responsive frequencies of the gas mixture;
   a transmit antenna coupled to said at least one microwave generator, said transmit antenna configured to transmit an electromagnetic energy emission spectrum through the gas mixture in a response to a microwave radiation coupled to said transmit antenna from said at least one microwave generator;
   a receive antenna spaced from said transmit antenna so that the gas mixture flows between said transmit antenna and said receive antenna, said receive antenna configured to capture an electromagnetic energy difference between said electromagnetic energy emission spectrum transmitted from said transmit antenna and an electromagnetic energy emission spectrum being absorbed or reflected by gaseous molecules in the gas mixture;
   a receiver coupled to said receive and/or transmit antenna, said receiver configured to convert said electromagnetic energy difference into a digital signal; and
   a control member configured to process said digital signal in accordance with one or more algorithms, said control member configured to analyze said electromagnetic energy difference and determine concentration(s) of gasses in the gas mixture based on an analysis of said electromagnetic energy difference.

2. The apparatus of claim 1, wherein said control member is configured to identify a presence or an absence of a heart failure condition in a subject in a response to measuring concentrations of at least one of Acetone, Pentane, Hexane, Propane, NO+, Oxygen, Nitrogen, and Carbon Dioxide and computationally combining the concentrations measured into an overall score indicative of a degree of or a probability of the heart failure condition in the subject.

3. The apparatus of claim 1, wherein said control member is configured to identify a presence or an absence of a Pneumonia condition in a subject in a response to measuring concentrations of gasses being any one of Isoprene, Hydrogen Cyanide, Oxygen, Nitrogen, and Carbon Dioxide and computationally combining the concentrations measured into an overall score indicative of a degree of or probability of the Pneumonia condition in the subject.

4. The apparatus of claim 1 wherein said control member is configured to identify a presence or an absence of a Pulmonary Oxygen Toxicity condition in a subject in a response to measuring the concentrations of gasses being any one of 3-meythyltridecane, 3-methyltridecane, 5-methylnonane, Oxygen, Nitrogen, and Carbon Dioxide and computationally combining the concentrations measured into an overall score indicative of a degree of or probability of the Pulmonary Oxygen Toxicity condition in the subject.

5. An apparatus of claim 1, wherein said control member is configured to determine a relationship between a concentration of gas compounds.

6. An apparatus of claim 1, wherein said control member is configured to determine an intensity of compound absorption or reflection spectrum in a form of a calibration curve.

7. An apparatus of claim 1, wherein said control member is configured to subject said electromagnetic energy emission spectrum to a Fourier analysis.

8. The apparatus of claim 1, wherein said microwave generator includes at least one of a microwave synthesizer, a directional coupler, a circulator, and a microwave amplifier connected to an output of said microwave synthesizer.

9. The apparatus of claim 1, wherein said control member comprises at least one of a non-coherent and a coherent integration signal processing to increase a sensitivity of said apparatus.

10. The apparatus of claim 9, wherein said sensitivity is below −149 dBm.

11. The apparatus of claim 1, wherein a microwave radiation level emitted from said microwave generator is maintained below a Specific Absorption Rate (SAR) mandated in accordance with a predefined standard for a person wearing said apparatus where said apparatus is operable as a measurement device.

12. The apparatus of claim 1, wherein said transmit antenna being further configured to receive an electromagnetic energy emission spectrum reflected by the gas mixture, said receiver being further configured to receive electromagnetic energy emission spectrum reflected by the gas mixture and received by said transmit antenna and convert said reflected electromagnetic energy emission spectrum into said digital signal.

13. The apparatus of claim 1, wherein each of said receive antenna and said transmit antenna disposed within said hollow enclosure.

14. The apparatus of claim 1, wherein said hollow enclosure comprises a Faraday Cage.

15. The apparatus of claim 1, further comprising a thermistor, said thermistor outputting a voltage signal in a response to measuring temperature of the gas mixture evacuated through said evacuation member.

16. The apparatus of claim 1, further comprising three sensors, each of said three sensors outputting a voltage signal in a response to respectively measuring oxygen, nitrogen, and carbon dioxide levels of the gas mixture evacuated through said evacuation member.

17. An apparatus for determining a concentration of gasses in a gas mixture, said apparatus comprising:
   a hollow enclosure;
   an intake member attached to said hollow enclosure, said intake member configured to introduce the gas mixture into said hollow enclosure;
   an evacuation member attached to said hollow enclosure, said evacuation member configured to evacuate the gas mixture from said hollow enclosure;
   at least one microwave generator tuned to responsive frequencies of the gas;
   a transmit antenna coupled to said at least one microwave generator, said transmit antenna configured to transmit an electromagnetic energy emission spectrum through the gas mixture in a response to a microwave radiation coupled to said transmit antenna from said at least one microwave generator;
   a receive antenna spaced from said transmit antenna so that the gas mixture flows between said transmit antenna and said receive antenna, said receive antenna configured to capture an electromagnetic energy difference between said electromagnetic energy emission spectrum transmitted from said transmit antenna and an electromagnetic energy emission spectrum being absorbed or reflected by gaseous molecules in the gas mixture;
   a receiver coupled to said receive and/or transmit antenna, said receiver configured to convert said electromagnetic energy difference into a digital signal; and
   a control member configured to
      measure, in said digital signal, at least one of an absorption amplitude, an emission amplitude and a reflection amplitude,
      convert said at least one of said absorption amplitude, said emission amplitude and said reflection amplitude to an absolute concentration, and
      compare said absolute concentration against a stored value.

* * * * *